(12) United States Patent
Sauer et al.

(10) Patent No.: US 10,524,964 B2
(45) Date of Patent: Jan. 7, 2020

(54) ABSORBENT ARTICLE WITH WAISTBAND

(71) Applicant: The Procter & Gamble Company, Cincinnati, OH (US)

(72) Inventors: Andrew James Sauer, Cincinnati, OH (US); Jeromy Thomas Raycheck, South Lebanon, OH (US); Mark James Kline, Okeana, OH (US); Kathleen Marie Lawson, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 649 days.

(21) Appl. No.: 14/533,472

(22) Filed: Nov. 5, 2014

(65) Prior Publication Data

US 2015/0126955 A1 May 7, 2015

Related U.S. Application Data

(60) Provisional application No. 61/900,072, filed on Nov. 5, 2013.

(51) Int. Cl.
*A61F 13/15* (2006.01)
*A61F 13/56* (2006.01)
*A61F 13/49* (2006.01)
*A61F 13/62* (2006.01)

(52) U.S. Cl.
CPC .... *A61F 13/5633* (2013.01); *A61F 13/49011* (2013.01); *A61F 13/5638* (2013.01); *A61F 13/62* (2013.01); *A61F 2013/49028* (2013.01)

(58) Field of Classification Search
CPC ............ A61F 13/49011; A61F 13/5633; A61F 13/5638; A61F 13/62; A61F 2013/49028
See application file for complete search history.

(56) References Cited

U.S. PATENT DOCUMENTS

| | | |
|---|---|---|
| 3,260,778 A | 7/1966 | Walton |
| 3,848,594 A | 11/1974 | Buell |
| 3,860,003 A | 1/1975 | Buell |
| 4,041,203 A | 8/1977 | Brock et al. |
| 4,081,301 A | 3/1978 | Buell |
| 4,090,385 A | 5/1978 | Packard |
| 4,205,679 A | 6/1980 | Repke et al. |

(Continued)

FOREIGN PATENT DOCUMENTS

| | | |
|---|---|---|
| JP | 2006-122456 | 5/2006 |
| JP | 2008-173286 | 7/2008 |

(Continued)

OTHER PUBLICATIONS

PCT International Search Report, dated Feb. 5, 2015 (10 pages).

(Continued)

*Primary Examiner* — Bradley H Philips
(74) *Attorney, Agent, or Firm* — Daniel S. Albrecht; William E. Gallagher; Andrew J. Mueller

(57) ABSTRACT

A disposable absorbent article is disclosed that includes a first waist region, a second waist region, a crotch region disposed between the first waist region and second waist region, a waist edge in the first waist region, at least one waistband in the first waist region adjacent the waist edge, at least one fastener in the second waist region, and a waist assembly in the first waist region, wherein the waist assembly has a Corrugation Regularity greater than about 75%.

25 Claims, 17 Drawing Sheets

(56) References Cited

U.S. PATENT DOCUMENTS

| | | |
|---|---|---|
| 4,284,454 A | 8/1981 | Joa |
| 4,300,967 A | 11/1981 | Sigl |
| 4,515,595 A | 5/1985 | Kievet et al. |
| 4,552,795 A | 11/1985 | Hansen et al. |
| 4,574,022 A | 3/1986 | Johnson et al. |
| 4,610,678 A | 9/1986 | Weisman et al. |
| 4,662,875 A | 5/1987 | Hirotsu et al. |
| 4,673,402 A | 6/1987 | Weisman et al. |
| 4,699,622 A | 10/1987 | Toussant et al. |
| 4,743,241 A | 5/1988 | Igaue et al. |
| 4,808,252 A | 2/1989 | Lash |
| 4,834,735 A | 5/1989 | Alemany et al. |
| 4,846,815 A | 7/1989 | Scripps |
| 4,854,984 A | 8/1989 | Ball et al. |
| 4,883,549 A | 11/1989 | Frost et al. |
| 4,888,231 A | 12/1989 | Angstadt |
| 4,892,536 A | 1/1990 | DesMarais et al. |
| 4,894,060 A | 1/1990 | Nestegard |
| 4,946,527 A | 8/1990 | Battrell |
| 4,963,140 A | 10/1990 | Robertson et al. |
| 4,977,011 A | 12/1990 | Smith |
| 4,990,147 A | 2/1991 | Freeland |
| 5,037,416 A | 8/1991 | Allen et al. |
| 5,137,537 A | 8/1992 | Herron et al. |
| 5,147,345 A | 8/1992 | Herron et al. |
| 5,151,092 A | 9/1992 | Buell et al. |
| 5,156,793 A | 10/1992 | Buell et al. |
| 5,167,897 A | 12/1992 | Weber et al. |
| 5,196,000 A | 3/1993 | Clear et al. |
| 5,209,801 A | 5/1993 | Smith |
| 5,221,274 A | 6/1993 | Buell et al. |
| 5,242,436 A | 9/1993 | Weil et al. |
| 5,260,345 A | 11/1993 | DesMarais et al. |
| 5,269,775 A | 12/1993 | Freeland et al. |
| 5,342,338 A | 8/1994 | Roe |
| 5,344,516 A | 9/1994 | Tanji et al. |
| 5,364,382 A | 11/1994 | Latimer et al. |
| 5,387,207 A | 2/1995 | Dyer et al. |
| 5,397,316 A | 3/1995 | Lavon et al. |
| 5,415,649 A | 5/1995 | Watanabe et al. |
| 5,429,629 A | 7/1995 | Latimer et al. |
| 5,499,978 A | 3/1996 | Buell et al. |
| 5,500,063 A | 3/1996 | Jessup |
| 5,507,736 A | 4/1996 | Clear et al. |
| 5,545,158 A | 8/1996 | Jessup |
| 5,554,143 A | 9/1996 | Roe et al. |
| 5,554,145 A | 9/1996 | Roe et al. |
| 5,569,234 A | 10/1996 | Buell et al. |
| 5,571,096 A | 11/1996 | Dobrin et al. |
| 5,576,090 A | 11/1996 | Suzuki |
| 5,580,411 A | 12/1996 | Nease et al. |
| 5,591,152 A | 1/1997 | Buell et al. |
| 5,635,191 A | 1/1997 | Roe et al. |
| 5,607,760 A | 3/1997 | Roe |
| 5,609,587 A | 3/1997 | Roe |
| 5,620,545 A | 4/1997 | Braun et al. |
| 5,622,581 A | 4/1997 | Ducker et al. |
| 5,625,222 A | 4/1997 | Yoneda et al. |
| 5,626,574 A | 5/1997 | Sasaki et al. |
| 5,643,588 A | 7/1997 | Roe et al. |
| 5,653,704 A | 8/1997 | Buell |
| 5,681,302 A | 10/1997 | Melbye et al. |
| 5,735,839 A | 4/1998 | Kawaguchi et al. |
| 5,749,865 A | 5/1998 | Yamamoto et al. |
| 5,827,259 A | 10/1998 | Laux et al. |
| 5,843,057 A | 12/1998 | McCormack |
| 5,865,823 A | 2/1999 | Curro |
| 5,914,084 A | 6/1999 | Benson et al. |
| 5,928,211 A | 7/1999 | Gustafsson et al. |
| 5,941,865 A | 8/1999 | Otsubo et al. |
| 6,004,306 A | 12/1999 | Robles et al. |
| 6,017,406 A * | 1/2000 | Vogt ................ A61F 13/15593 |
| | | 156/164 |
| 6,027,593 A | 2/2000 | Lunt et al. |
| 6,096,668 A | 8/2000 | Abuto et al. |
| 6,107,537 A | 8/2000 | Elder et al. |
| 6,120,487 A | 9/2000 | Ashton |
| 6,248,097 B1 | 6/2001 | Beitz et al. |
| 6,264,643 B1 | 7/2001 | Toyoda |
| 6,375,646 B1 | 4/2002 | Widlund et al. |
| 6,383,431 B1 | 5/2002 | Dobrin et al. |
| 6,432,098 B1 | 8/2002 | Kline et al. |
| 6,436,216 B1 | 8/2002 | Grover |
| 6,458,447 B1 | 10/2002 | Cabell et al. |
| 6,537,644 B1 | 3/2003 | Kauschke et al. |
| 6,537,936 B1 | 3/2003 | Busam et al. |
| 6,595,976 B2 | 7/2003 | Jitoe et al. |
| 6,729,669 B2 | 5/2004 | McManus et al. |
| 6,808,582 B2 | 10/2004 | Popp et al. |
| 6,884,310 B2 | 4/2005 | Roessler et al. |
| 6,902,793 B2 | 6/2005 | Ukegawa et al. |
| 7,029,545 B2 | 4/2006 | Suzuki |
| 7,037,300 B2 | 5/2006 | Kling |
| 7,108,759 B2 | 9/2006 | You et al. |
| 7,112,193 B2 | 9/2006 | Otsubo |
| 7,118,558 B2 | 10/2006 | Wu et al. |
| 7,255,688 B2 | 8/2007 | Sasaki et al. |
| 7,291,138 B2 | 11/2007 | Hoshino et al. |
| 7,329,245 B2 | 2/2008 | Torigoshi et al. |
| 7,331,946 B2 | 2/2008 | Shimada et al. |
| 7,361,802 B2 | 4/2008 | Ishikawa et al. |
| 7,407,557 B2 | 8/2008 | Wada et al. |
| 7,449,015 B2 | 11/2008 | Otsubo et al. |
| 7,465,367 B2 | 12/2008 | Day |
| 7,530,972 B2 | 5/2009 | Ando et al. |
| 7,569,039 B2 | 8/2009 | Matsuda et al. |
| 7,582,348 B2 | 9/2009 | Ando et al. |
| 7,601,657 B2 * | 10/2009 | Zhou ................ A61F 13/49009 |
| | | 442/327 |
| 7,621,900 B2 | 11/2009 | Van Gompel et al. |
| 7,642,398 B2 | 1/2010 | Jarpenberg et al. |
| 7,682,686 B2 | 3/2010 | Curro et al. |
| 7,744,576 B2 | 6/2010 | Busam et al. |
| 7,744,579 B2 | 6/2010 | Langdon et al. |
| 7,750,203 B2 | 7/2010 | Becker et al. |
| 7,754,040 B2 | 7/2010 | Norrby |
| 7,754,627 B2 | 7/2010 | Mukai et al. |
| 7,763,339 B2 | 7/2010 | Groitzsch et al. |
| 7,834,236 B2 | 11/2010 | Middlesworth et al. |
| 7,895,718 B2 | 3/2011 | Horn et al. |
| 8,038,662 B2 | 10/2011 | Homung et al. |
| 8,043,274 B2 | 10/2011 | Minar et al. |
| 8,082,636 B2 | 12/2011 | Miyamoto et al. |
| 8,333,749 B2 | 12/2012 | Tsang et al. |
| 8,348,918 B2 | 1/2013 | Langdon et al. |
| 8,348,919 B2 | 1/2013 | Langdon et al. |
| 8,377,023 B2 | 2/2013 | Sawyer et al. |
| 8,388,596 B2 | 3/2013 | Horn et al. |
| 8,450,556 B2 | 5/2013 | Miyamoto et al. |
| 8,475,424 B2 | 7/2013 | Fujimoto et al. |
| 8,496,638 B2 | 7/2013 | Lord et al. |
| 8,551,064 B2 | 10/2013 | Lavon et al. |
| 8,574,211 B2 | 11/2013 | Morita et al. |
| 8,597,268 B2 | 12/2013 | Sauer et al. |
| 8,647,319 B2 | 2/2014 | Een et al. |
| 9,011,404 B2 | 4/2015 | Kobayashi et al. |
| 9,216,116 B2 | 12/2015 | Roe et al. |
| D748,932 S | 2/2016 | Puricelli |
| 9,301,881 B2 | 4/2016 | Ando et al. |
| 9,326,899 B2 | 5/2016 | Zink et al. |
| 9,333,119 B2 | 5/2016 | Zink et al. |
| 9,375,361 B2 | 6/2016 | Zink et al. |
| 9,510,979 B2 | 12/2016 | Trennepohl et al. |
| 9,867,740 B2 | 1/2018 | Zink et al. |
| 2002/0049421 A1 | 4/2002 | Hayase et al. |
| 2002/0113042 A1 | 4/2002 | Tachibana et al. |
| 2002/0128626 A1 | 9/2002 | Friderich et al. |
| 2002/0177829 A1 | 11/2002 | Fell et al. |
| 2003/0023220 A1 | 1/2003 | Ukegawa et al. |
| 2003/0031834 A1 * | 2/2003 | Ukegawa ......... A61F 13/49011 |
| | | 428/174 |
| 2004/0015146 A1 | 1/2004 | Torigoshi et al. |
| 2004/0102757 A1 | 5/2004 | Olson |
| 2004/0127876 A1 | 7/2004 | Stevens |

(56) References Cited

U.S. PATENT DOCUMENTS

| | | |
|---|---|---|
| 2004/0243085 A1 | 12/2004 | Veith et al. |
| 2005/0004549 A1 | 1/2005 | Maas et al. |
| 2005/0203479 A1 | 3/2005 | Sakaguchi |
| 2005/0215155 A1 | 9/2005 | Young et al. |
| 2006/0069361 A1 | 3/2006 | Olson |
| 2006/0142728 A1 | 6/2006 | Tabor et al. |
| 2006/0173436 A1 | 8/2006 | Patsy |
| 2006/0270302 A1* | 11/2006 | Ando .................. A61F 13/4902 442/328 |
| 2007/0249253 A1 | 10/2007 | Angeli |
| 2008/0009817 A1 | 1/2008 | Norrby |
| 2008/0124996 A1 | 5/2008 | Hashimoto |
| 2008/0312617 A1 | 12/2008 | Hundorf et al. |
| 2009/0035527 A1 | 2/2009 | Kobayashi |
| 2009/0061185 A1 | 3/2009 | Hisamoto |
| 2009/0157035 A1 | 6/2009 | Ponomarenko |
| 2009/0182298 A1 | 7/2009 | Kumasaka |
| 2009/0191779 A1 | 7/2009 | Cree |
| 2009/0264852 A1* | 10/2009 | Miyamoto .......... A61F 13/5638 604/386 |
| 2009/0275909 A1 | 11/2009 | Sakaguchi |
| 2009/0308524 A1 | 12/2009 | Gunji |
| 2009/0326499 A1 | 12/2009 | Veith |
| 2010/0076394 A1 | 3/2010 | Hayase |
| 2010/0234823 A1* | 9/2010 | Morita ................ A61F 13/4902 604/385.22 |
| 2010/0286646 A1 | 11/2010 | Takino |
| 2010/0312214 A1 | 12/2010 | Shimada et al. |
| 2010/0318054 A1 | 12/2010 | Langdon et al. |
| 2011/0022019 A1 | 1/2011 | Shimada et al. |
| 2011/0071488 A1 | 3/2011 | Kuwano et al. |
| 2011/0106039 A1 | 5/2011 | Saito et al. |
| 2011/0118689 A1* | 5/2011 | Een .................. A61F 13/49011 604/385.3 |
| 2011/0144610 A1 | 6/2011 | Kalson et al. |
| 2011/0172626 A1 | 7/2011 | Mitsuno |
| 2011/0178489 A1 | 7/2011 | Baba et al. |
| 2011/0213325 A1 | 9/2011 | Gabrielli et al. |
| 2011/0251576 A1 | 10/2011 | Ando et al. |
| 2012/0041407 A1 | 2/2012 | Kamiyama et al. |
| 2012/0251771 A1 | 10/2012 | Wilson |
| 2012/0277702 A1* | 11/2012 | Raycheck ......... A61F 13/51496 604/367 |
| 2012/0277713 A1* | 11/2012 | Raycheck ........... A61F 13/4942 604/385.26 |
| 2012/0289921 A1 | 11/2012 | Hashino et al. |
| 2012/0330236 A1 | 12/2012 | Lawson et al. |
| 2012/0330262 A1 | 12/2012 | Lawson et al. |
| 2012/0330264 A1 | 12/2012 | Lawson et al. |
| 2013/0006207 A1 | 1/2013 | Roe et al. |
| 2013/0041340 A1 | 2/2013 | Kawakami et al. |
| 2013/0261589 A1 | 10/2013 | Fujkawa |
| 2013/0306226 A1 | 11/2013 | Zink et al. |
| 2015/0126956 A1 | 5/2015 | Raycheck et al. |
| 2016/0058624 A1 | 3/2016 | Hohm |
| 2016/0220425 A1 | 8/2016 | Zink et al. |
| 2016/0235599 A1 | 8/2016 | Zink et al. |
| 2018/0092785 A1 | 4/2018 | Zink et al. |

FOREIGN PATENT DOCUMENTS

| | | |
|---|---|---|
| JP | 2009-240694 | 10/2009 |
| JP | 5102119 | 12/2012 |
| WO | WO 1995-16746 A1 | 6/1995 |
| WO | WO2000037003 | 6/2000 |

OTHER PUBLICATIONS

All Office Actions for U.S. Appl. No. 14/533,511.
All Office Actions for U.S. Appl. No. 13/893,405.
All Office Actions for U.S. Appl. No. 15/088,197.
All Office Actions for U.S. Appl. No. 15/833,166.
All Office Actions for U.S. Appl. No. 13/893,634.
All Office Actions for U.S. Appl. No. 15/088,207.
All Office Actions for U.S. Appl. No. 13/893,658.
All Office Actions for U.S. Appl. No. 15/137,041.
All Office Actions for U.S. Appl. No. 13/893,735.

* cited by examiner

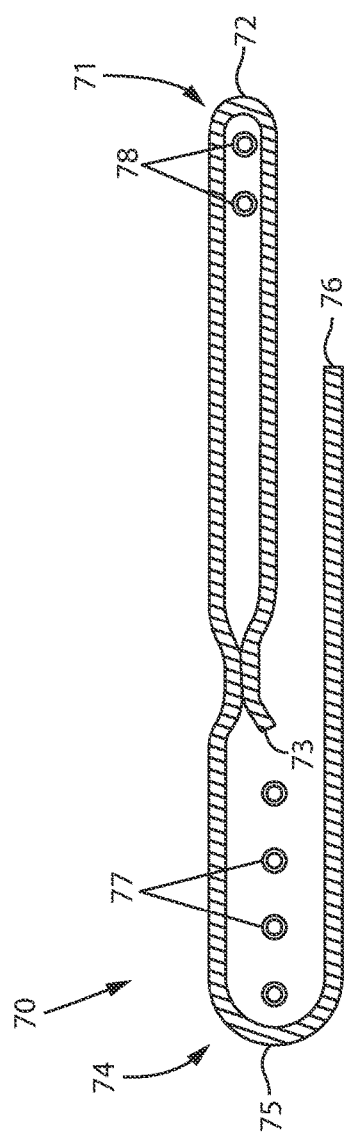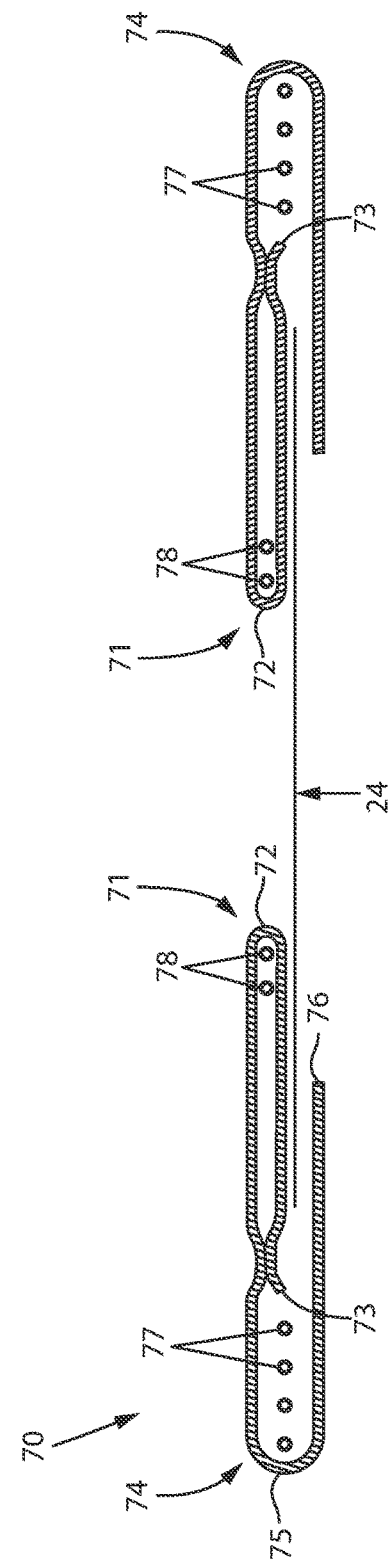

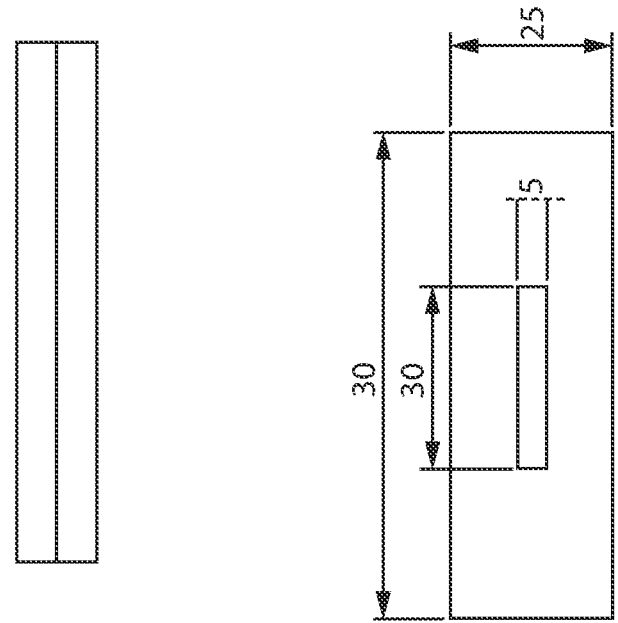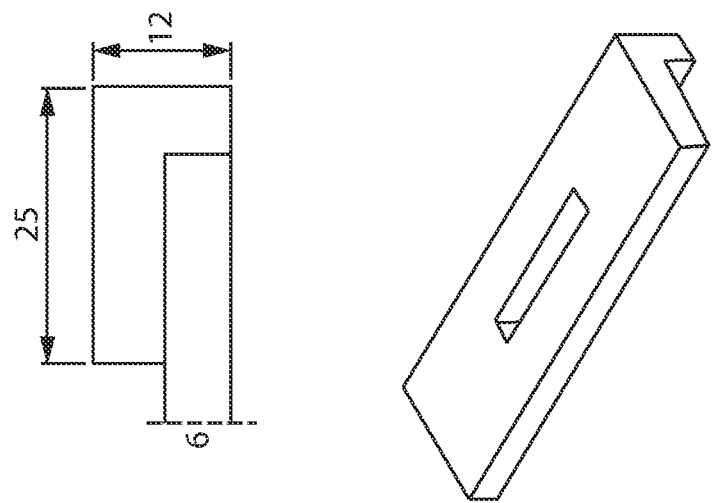
Fig. 10

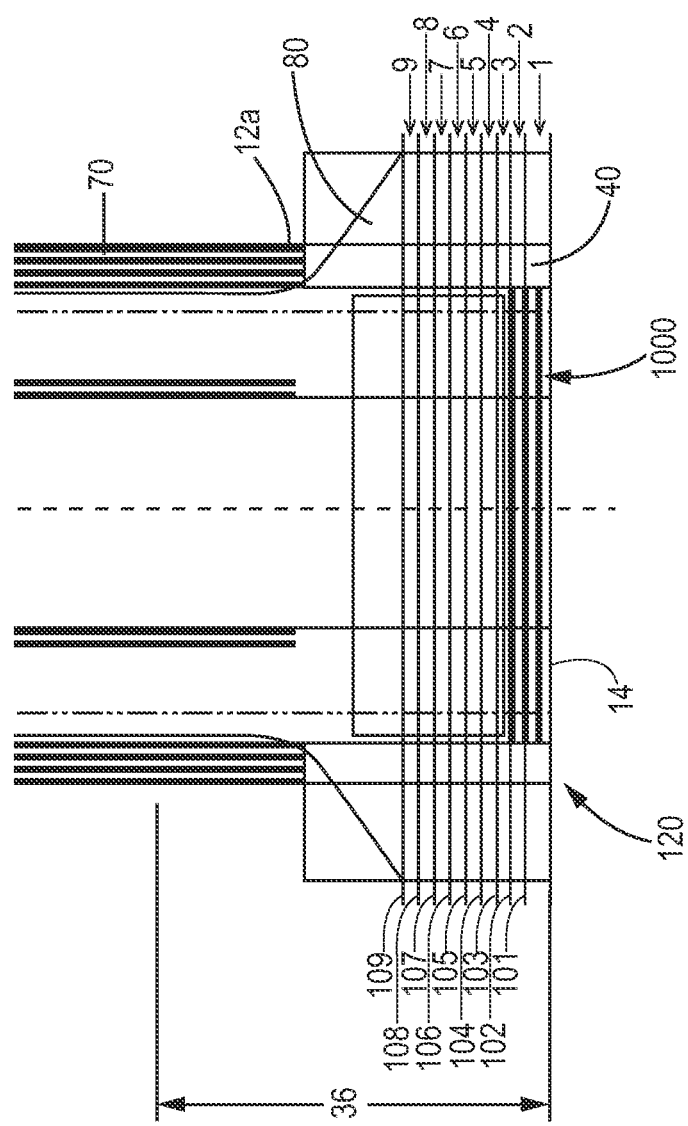

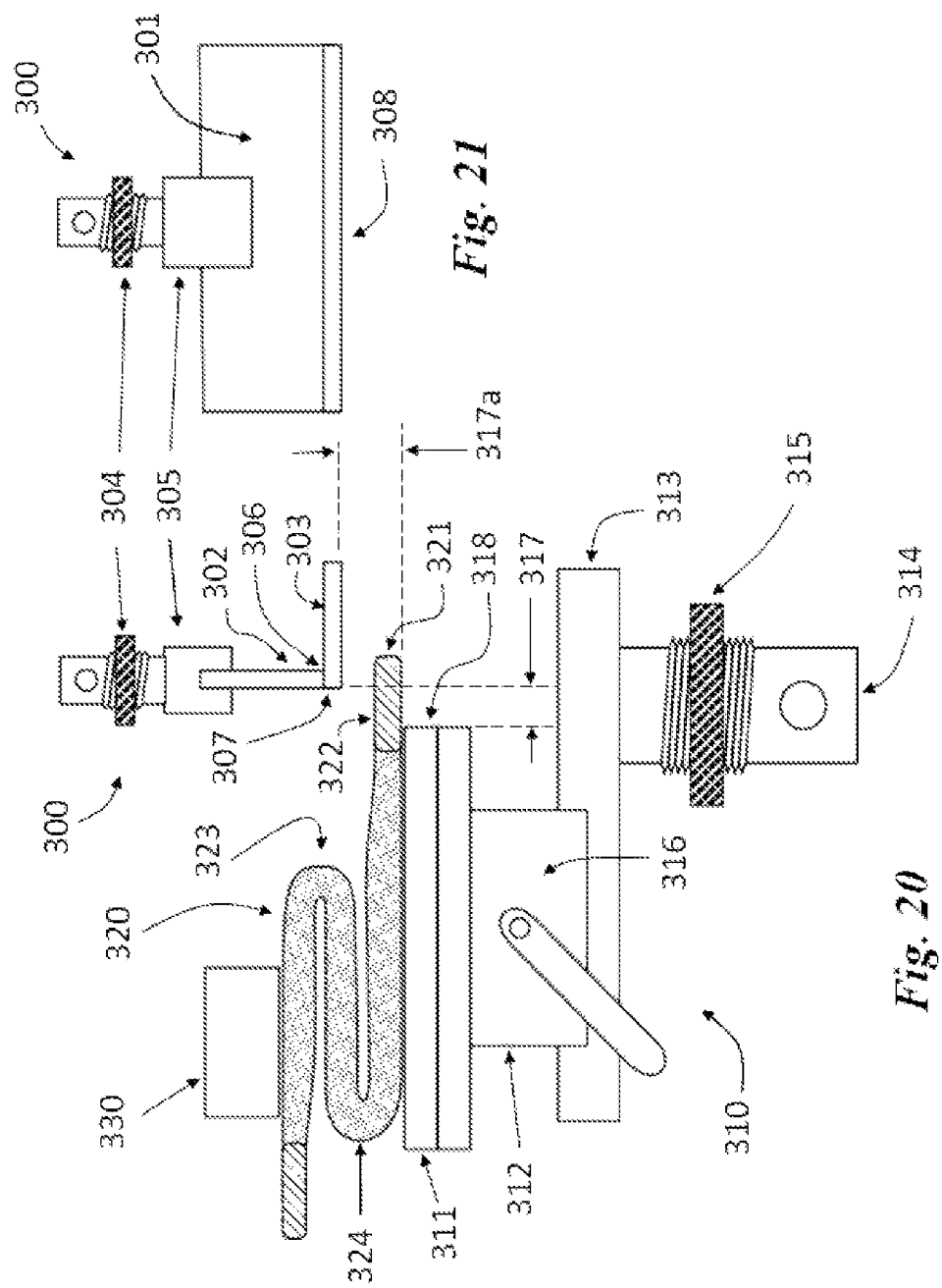

ABSORBENT ARTICLE WITH WAISTBAND

FIELD OF INVENTION

This disclosure relates to open form disposable absorbent articles, such as diapers, having improved waistband properties that yield a more underwear-like article. The absorbent article may have improved functional characteristics and communicative properties.

BACKGROUND OF THE INVENTION

Disposable absorbent articles which have a conforming, underwear-like fit are more desirable for moms and babies because it allows them to aspire to a time when the baby will be potty trained and no longer in diapers. Thus, an absorbent product that can deliver an underwear-like perception is more desirable than one that does not. A common feature among underwear is a continuous stretchable waistband along the top of the product, which allows the top of the underwear to resist rolling, flipping and/or scrunching during wear. Said another way, the continuous stretchable waistband promotes continuous contact between the top of the underwear and the wearer's body. This promotion of continuous contact may be achieved because the waistband is configured to have continuous tension at the top edge of the underwear. Accordingly, the continuous stretchable waistband makes it energetically unfavorable for any particular portion of the waistband to move away from the surface of the body (e.g., roll, flip and/or scrunch). In addition, if any portion of continuous stretchable waistband does move away from the surface of the body, the continuous stretchable waistband also makes it energetically favorable for the waistband to return to its original position in contact with the wearer's body.

Many disposable absorbent articles are configured in an open form (e.g., taped diapers) so they can be fastened around a wearer's torso and adjusted accordingly. This structure may allow for easy application and removal of the absorbent articles, may be less expensive to manufacture versus pant type absorbent articles, and allows the products to fit a wider range of wearers with different body shapes and sizes. Despite being an open form product, it is still desirable for the product to be perceived like underwear for the reasons stated above. Open form absorbent articles, however, do not have a continuous stretchable waistband which encircles the waist of the wearer. Thus, when stretchable materials are employed on an open form disposable absorbent article in a waist region (e.g., a front waist feature such as a front waistband), such materials often do not maintain continuous contact with the wearer's body and roll, flip and/or scrunch during wear. As an example, this phenomenon can often be seen when a taped diaper being worn by a baby has the top front region above the tape fasteners flipped over and not in contact with the baby's stomach.

Prior solutions to rolling, flipping and/or scrunching of the front waist region of an open form disposable absorbent article have included additional fastening elements to secure the loose ends of the front of the product. Fastening elements, however, increase cost and risk irritating the wearer's skin. Further, when used with stretch elements or a non-stretchable waist region, additional fastening elements can create a fit which limits the stretch and is tight and uncomfortable for a wearer. Other proposed solutions have included regions of high stiffness to provide additional support to the waist region of the product. The high stiffness in the waist region resists the bending or buckling force exerted by the wearer. However, the high stiffness also results in a front waist region which does not conform to the body of the wearer as the body continuously changes shape during use due to a wearer's posture, breathing, food intake, etc., and therefore is uncomfortable for the wearer.

It is thus desirable to have a front waist region with a stretchable front waist feature (e.g., a front waistband) in an open form disposable absorbent article which is inexpensive to manufacture, wherein the front waist region is flexible and comfortable to wear, promotes continuous contact with the wearer's body, resists rolling, flipping or scrunching, and if the front waist region does roll, flip or scrunch, has a tendency to return to its original position in contact with the wearer's body.

SUMMARY OF THE INVENTION

In one embodiment, the open form disposable absorbent articles detailed herein include a first waist region, a second waist region, a crotch region disposed between the first waist region and second waist region, a waist edge in the first waist region, at least one waistband in the first waist region adjacent the waist edge, and at least one fastener in the second waist region, wherein the first waist region has a resiliency of greater than about 5 mJ and a stiffness of less than about 10 N.

In another embodiment, the open form disposable absorbent articles detailed herein include a first waist region, a second waist region, a crotch region disposed between the first waist region and second waist region, a waist edge in the first waist region, at least one waistband in the first waist region adjacent the waist edge, and at least one ear in the second waist region, wherein the first waist region has a first section, a second section, a third section, a fourth section, a fifth section, a sixth section, a seventh section, an eighth section and a ninth section, wherein the stiffness of the second section is less than about 10 N, and wherein the difference in resiliency between two adjacent sections is not more than about 60% of the average resiliency of all of the sections.

In another embodiment, the open form disposable absorbent articles detailed herein include a first waist region, a second waist region, a crotch region disposed between the first waist region and second waist region, a waist edge in the first waist region, at least one waistband in the first waist region adjacent the waist edge, at least one fastener in the second waist region, and a waist assembly in the first waist region, wherein the waist assembly has a Corrugation Regularity greater than about 75%.

In another embodiment, the open form disposable absorbent articles detailed herein include a first waist region, a second waist region, a crotch region disposed between the first waist region and second waist region, a waist edge in the first waist region, at least one waistband in the first waist region adjacent the waist edge, at least one fastener in the second waist region, and a waist assembly in the first waist region; wherein the waist assembly has a Corrugation Uniformity of greater than about 50%.

In another embodiment, the open form disposable absorbent articles detailed herein include a first waist region, a second waist region, a crotch region disposed between the first waist region and second waist region, a waist edge in the first waist region, at least one waistband in the first waist region, at least one fastener in the second waist region, and at least one discrete landing zone in the first waist region, the discrete landing zone comprising an lateral inboard edge, wherein the discrete landing zone and the waistband overlap to form an overlap region in the first waist region, and wherein the waistband does not overlap the lateral inboard edge of the discrete landing zone.

In another embodiment, the open form disposable absorbent articles detailed herein include a first waist region, a second waist region, a crotch region disposed between the first waist region and second waist region, a waist edge in the first waist region, at least one waistband in the first waist region, at least one fastener in the second waist region, a topsheet, a backsheet, and an absorbent core disposed between the topsheet and backsheet, the absorbent core having a lateral edge disposed in the first waist region, said lateral edge of the core being inboard of the waist edge in the first waist region; wherein the absorbent core and the waistband overlap to form an overlap region in the first waist region.

BRIEF DESCRIPTION OF THE DRAWINGS

FIG. 4 is a schematic cross section view of an embodiment of a folded outer leg cuff suitable for use in the absorbent articles detailed herein.

FIG. 5 is a schematic cross section view of an embodiment of a folded outer leg cuff suitable for use in the absorbent articles detailed herein.

FIG. 10 is a schematic representation of a template.

FIG. 11 is an enlarged view of the front waist region of the exemplary open form disposable absorbent article of FIG. 1.

FIG. 20 is a schematic representation of a side view of a portion of the apparatus used to measure resiliency and stiffness as detailed herein.

FIG. 21 is a schematic representation of a front view of a portion of the apparatus used to measure resiliency and stiffness as detailed herein.

DETAILED DESCRIPTION OF THE INVENTION

Figure 1:
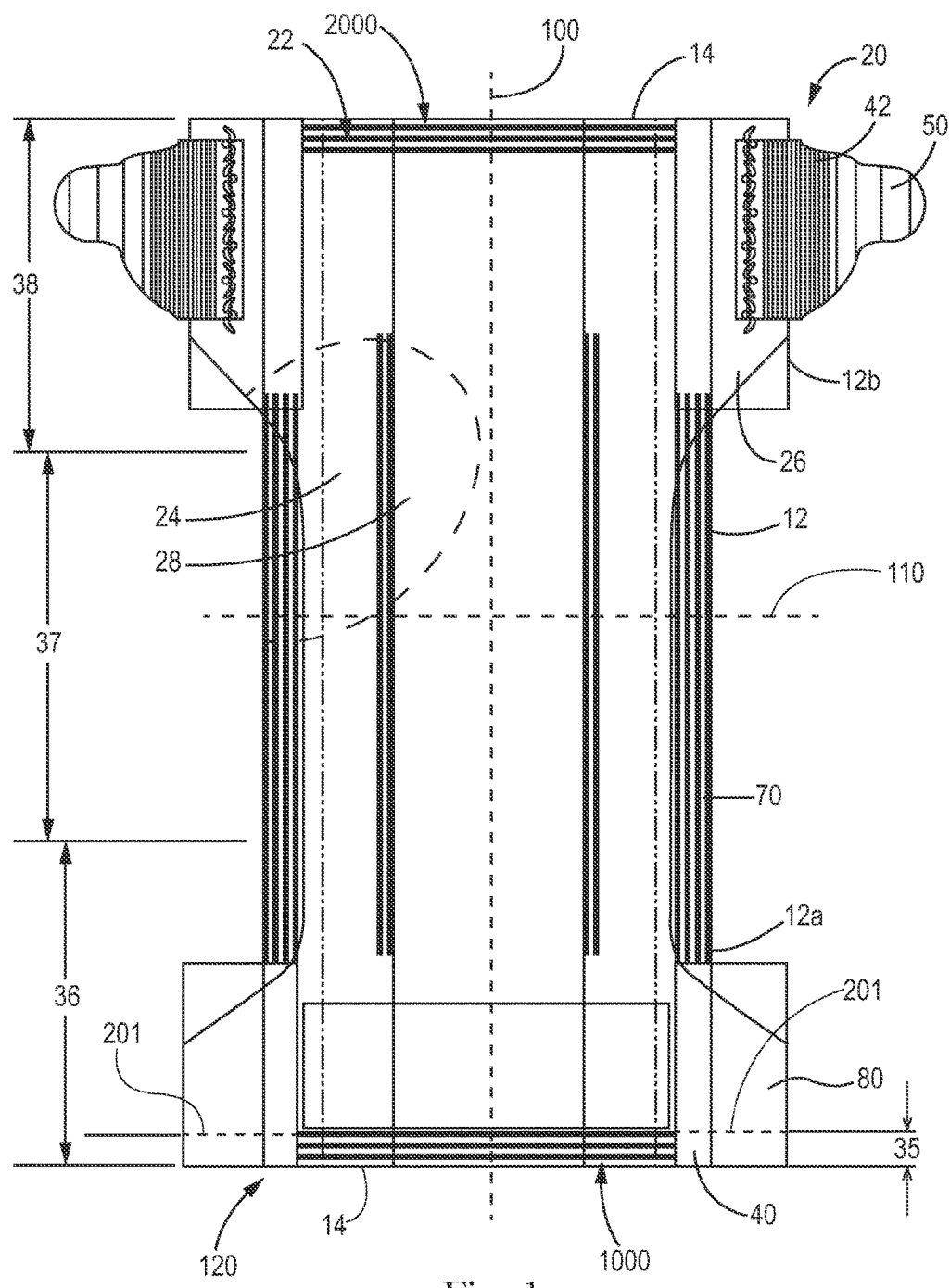
FIG. 1 is a plan view of an embodiment of the open form disposable absorbent articles detailed herein.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Inboard" and "Outboard" refer respectively to the location of an element relative a centerline (longitudinal or lateral) of the absorbent article. Inboard refers to a location closer to the centerline and outboard refers to a location further from the centerline.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Discrete landing zone" refers to a component of a fastening element, typically but not limited to, the female engaging portion of a hook and loop fastening system. The discrete landing zone is a discrete component that is attached to the garment facing surface of an open form disposable article.

"Elastomeric material" is a material exhibiting elastic properties. Elastomeric materials may include elastomeric films, strands, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Figure 3:
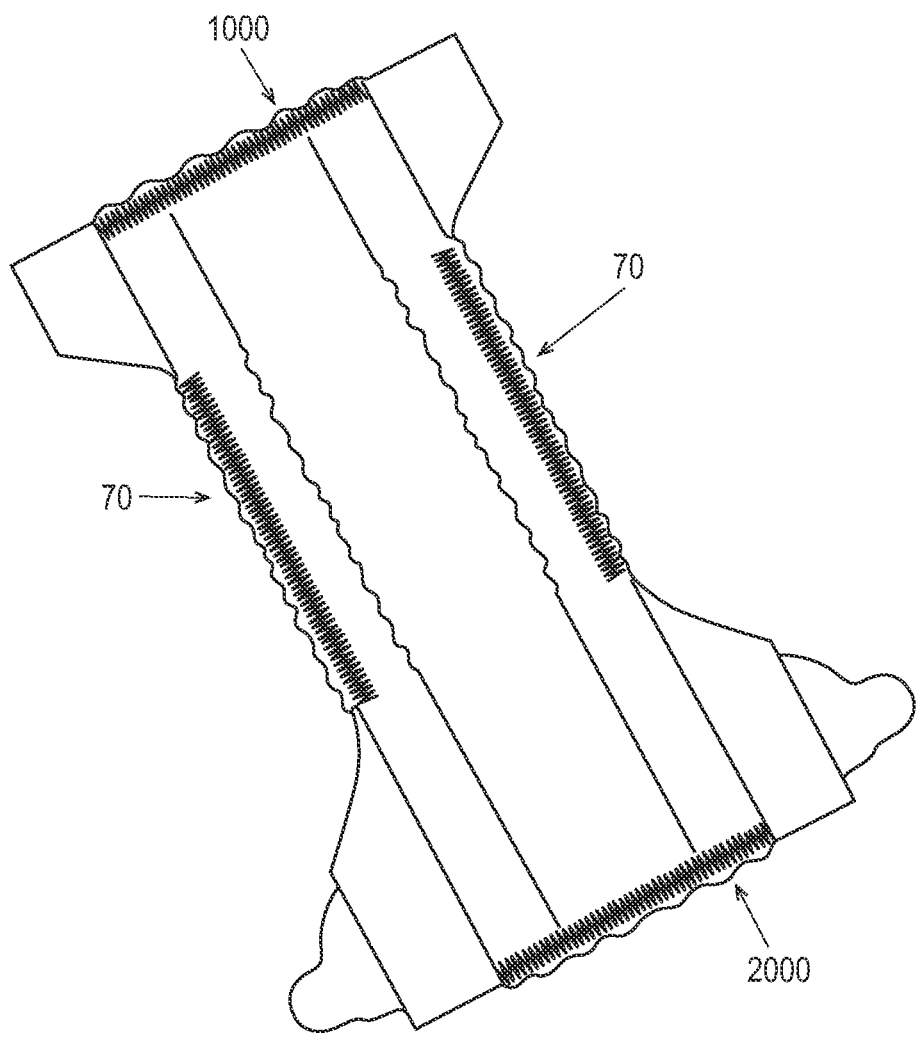
FIG. 3 is a plan view of an embodiment of the absorbent article detailed herein.

"Open form" refers to disposable absorbent articles which do not include pre-formed waist and leg openings, and employ fasteners to secure the diaper around the waist of the wearer. FIGS. 1 and 3 are illustrative examples of open form disposable absorbent articles.

"Corrugations" refers to wrinkles or deformations of a material in the z-axis (i.e., out of plane of the diaper in FIG. 1). Corrugations may be used interchangeably with the term "gathers."

"Regular corrugations" refers to corrugations which substantially occur at a single primary frequency. For example, one embodiment of regular corrugations is a set of corrugations that have a space between the peaks of the corrugations where no more than 25% of the spaces vary from the average spacing by more than plus or minus 1 mm.

A "uniform corrugation" refers to a corrugation which spans the longitudinal length of the waist assembly of the first waist region without being broken or disrupted, as further detailed in the method of calculating Corrugation Uniformity herein. A waist assembly is considered to be uniformly corrugated if at least one surface (e.g., body facing surface or garment facing surface) has more than 50% corrugations that are uniform corrugations.

"Waistband" refers to a discretely applied component in at least first waist region, and can be applied on the garment facing surface, the body facing surface, or sandwiched between layers of the absorbent article.

"Waist assembly" refers a general region of the absorbent article where a waistband could be discretely applied. This region generally includes multiple layers of the absorbent article, including but not limited to, topsheet, backsheet (microporous film and/or outer cover), discrete landing zone, absorbent assembly (or portions thereof), leg gasketing system, opacity strengthening patches, etc. If the absorbent article includes a waistband and the waistband is less than 25 mm long in the longitudinal direction, the waist assembly is defined as the area between the waist edge of the first waist region and the inboard edge of the waistband. If there is no waistband or the waistband of the absorbent article is more than 25 mm long in the longitudinal direction, this region is defined as the area between the waist edge of the first waist region and a line parallel to, and 25 mm inboard, of the waist edge of the first waist region.

FIG. 1 is a plan view of an exemplary, non-limiting embodiment of an open form disposable absorbent article 20 in a flat, uncontracted state (i.e., without elastic induced contraction). The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic elements such that they gather about the waist of the wearer to provide improved fit and containment. The waist regions 36 and 38 may include a first waistband 1000 and a second waistband 2000. The crotch region 37 is that portion of the absorbent article 20 which, when the absorbent article 20 is worn, is generally positioned between the legs of the wearer.

The outer periphery of chassis 22 is defined by longitudinal edges 12 and waist edges 14. The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing waist edges 14 that are oriented generally parallel to the lateral centerline 110.

The chassis 22 may comprise a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the absorbent article 20 with other features added to form the composite diaper structure. While the topsheet 24, the backsheet 26, and the absorbent core 28 may be assembled in a variety of well configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. The topsheet 24 may include apertures. One topsheet 24 useful herein is available from BBA Fiberweb, Brentwood, Tenn. as supplier code 055SLPV09U.

Any portion of the topsheet 24 may be coated with a lotion or skin care composition as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a core cover, a dusting layer, and a wide variety of liquid-absorbent materials commonly used in disposable diapers and other absorbent articles. The core cover and the dusting layer may be made from non-woven materials, or from any other material known in the art that can be employed as a core cover or a dusting layer. Some embodiments of the absorbent core do not include a core cover or a dusting layer.

Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores are described in greater details below.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the non-woven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the ear are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two non-woven layers (such as is available from BBA Fiberweb, Brentwood, Tenn. as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12. The integral ear may be formed by cutting the chassis form to include the shape of the ear projection.

The absorbent article 20 may also include a fastening system 50. When fastened, the fastening system 50 interconnects the first waist region 36 and the second waist region 38 resulting in a waist circumference that may encircle the wearer during wear of the absorbent article 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

Waistbands of the disposable absorbent articles detailed herein may result in absorbent articles having increased comfort, fit, and improved leakage performance for the wearer. Certain waistbands may also provide improved product durability and strength. The waistbands of the disposable absorbent articles detailed herein may also result an easier and improved absorbent article changing experience.

One object of the disposable absorbent articles detailed herein is to deliver an absorbent article having improved gap closure in the first and/or second waist regions of the absorbent article than what is currently known in the art today. Having gap closure in the waist regions may create an article with better fit and containment, resulting in improved leakage performance. One way to achieve gap closure is to provide a waistband that is flush coterminous with the rear waist edge of the absorbent article. Because there is variation in the application process, in some embodiments, a waistband may be present in both the first and second waist regions of the absorbent article. However, while a highly contracted waistband is desirable for the back waist region to provide gap closure, it may be more desirable to have a less contracted waistband in the front waist region to aid in application. Therefore, one embodiment of the disposable absorbent articles detailed herein is directed to "differential contraction" or waistband laminates having different installed elongation strands in the front versus the back, such that only one waistband laminate is cut. Cutting of the waistband laminate is subsequent to the waistband application to the article; the waistband is applied such that it spans the intended article separation (cut) zone. Thus, the same waistband laminate can deliver different levels of contraction in the back and front, resulting in higher contraction in the back to help close the gap and lower contraction in the front.

In one embodiment, the first (1000) and second waistbands (2000) are comprised of a waistband laminate (3000). In one embodiment, the waistband laminate is comprised of a nonwoven material (3100). In one embodiment, the waistband laminate is comprised of a film. In one embodiment, the waistband laminate is comprised of at least two elastic strands (3200), at least four elastic strands, at least six elastic strands, at least eight elastic strands, at least ten elastic strands, at least twelve elastic strands. Although the description and figures are mainly directed towards waistband laminates that include elastic strands, the teachings herein (e.g., material strains, elongations, ratios) are also applicable to waistband embodiments that contain elastomeric films, foams, or other stretchable materials used in waistband construction.

In one embodiment, the first and second waistbands are applied to the article at the same applied waistband strain. In one embodiment, the first waistband and the second waistband are applied to the disposable absorbent article at a strain of greater than about 30%, greater than about 50%, greater than about 70% as compared to the relaxed length. In one embodiment, the first waistband and the second waistband are applied to the disposable absorbent article at a strain of less than about 150%, less than about 125%, less than about 100%, less than about 75% as compared to the relaxed length. In one embodiment, the first waistband and the second waistband are applied to the disposable absorbent article at a strain of from about 70% to about 75% as compared to the relaxed length.

In one embodiment, the waistband laminate is comprised of a nonwoven material and at least two elastic strands, wherein each of the at least two elastic strands are different elastic materials. In one embodiment, the elastic strands may be round in cross section; however, other embodiments may have elastic strands of varying cross section geometries. In one embodiment, the elastic strands have different diameters or cross-sectional geometries.

Figure 2:
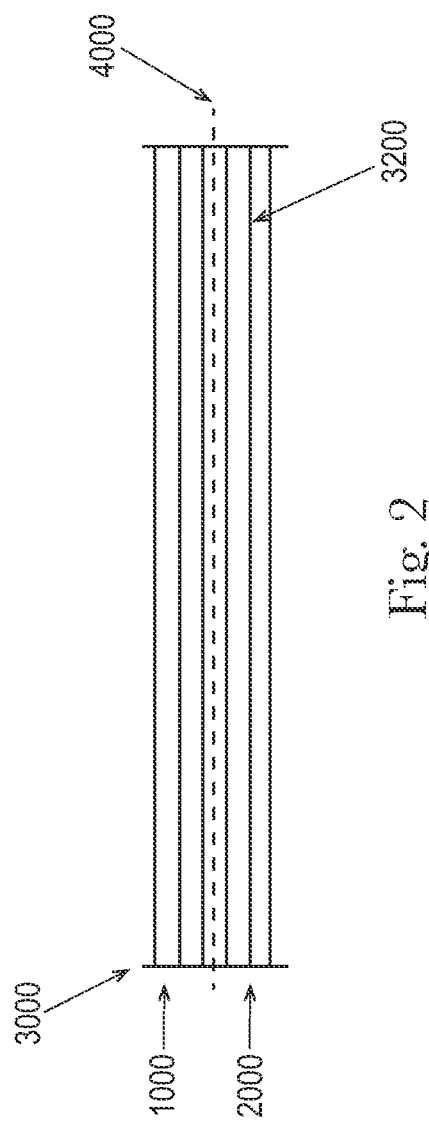
FIG. 2 is a plan view of an embodiment of a waistband laminate suitable for use in the absorbent articles detailed herein.

In one embodiment, the waistband laminate is cut after application to the article between the elastic strands such that a waistband laminate comprised of at least two elastic strands results in two waistbands each having one elastic strand; a waistband laminate comprised of at least four elastic strands results in two waistbands each having two elastic strands. As shown in FIG. 2, a waistband laminate 3000 comprised of at least six elastic strands results in two waistbands (1000, 2000) each having three elastic strands when cut (cut line 4000). Further, a waistband laminate comprised of at least eight elastic strands results in two waistbands each having four elastic strands, a waistband laminate comprised of at least ten elastic strands results in two waistbands each having five elastic strands, a waistband laminate comprised of at least twelve elastic strands results in two waistbands each having six elastic strands. In one embodiment, the waistband laminate is cut such that the two resulting waistbands have an unequal distribution of elastic strands or having no elastic strands on one side of the cut. For example, a waistband laminate having ten elastic strands may result in one waistband having six elastics and one waistband having four elastics. In another example, a waistband laminate having ten elastic strands may result in one waistband having ten elastics and one waistband having no elastics. In one embodiment, the waistband laminate is cut in the center to create the two waistbands. In one embodiment, the waistband laminate is cut off-center. In one embodiment, the waistband laminate may have elastic strands spaced equally apart. In one embodiment, the waistband laminate may have strands spaced closer together or further apart as compared to the other elastic strands in the laminate.

In one embodiment, the waistband has a length in the direction parallel to the longitudinal axis of the article of greater than about 12 mm, greater than about 15 mm, greater than about 20 mm. In one embodiment, the waistband has a length in the direction parallel to the longitudinal axis of the article of less than about 50 mm, less than about 45 mm, less than about 40 mm. In one embodiment, the waistband has a length in the direction parallel to the longitudinal axis of the article of about 25 mm.

In one embodiment, the waistband in a relaxed product has a length in the direction parallel to the lateral axis of the article of greater than about 50 mm, greater than about 75 mm, greater than about 100 mm. In one embodiment, the length in the direction parallel to the lateral axis of the article of the waistband in a relaxed product is less than about 300 mm, less than about 250 mm, less than about 200 mm.

In one embodiment, the CD Length Ratio of the waistband compared to the distance from one tape to the other tape is less than about 2, less than about 1.5, about 1.

In one embodiment, the waistband is on the body-facing surface of the article. In one embodiment, the waistband is on the garment-facing surface of the article. In one embodiment, the waistband is sandwiched in between the layers of the absorbent article. In one embodiment, the waistband is on the garment-facing surface in either the first or second waist regions and on the body-facing surface in either the first or second waist regions. In one embodiment, the waistband is on both the body-facing surface and the garment-facing surface. In one embodiment, the waistband is on either the body-facing surface or the garment-facing surface and the surface not comprising the waistband is printed with a printed waistband feature.

In one embodiment, when the waistband is in a relaxed state (i.e., the waistband is contracted), the distance from one tape edge to the other tape edge is at least about 50% the average length of the baby waist circumference for an average baby that wears the size of absorbent article; at least about 60% the average length; at least about 65% the average length.

In one embodiment, the elastic strands of the waistband laminate may have different installed elongations within one laminate, thus, after being cut, resulting in a first waistband having a first installed elongation and a second waistband having a second installed elongation; both the first and second waistbands have the same applied waistband strain. The installed elongation is the strain at which the elastic is under relative to the second material that it is combined with (e.g. low basis weight nonwoven). For example, if the elastic is stretched from 100 mm to 250 mm when it is combined with the nonwoven, it would be said to be 150% installed elongation or $((250 \text{ mm}/100 \text{ mm})-1) \times 100\%$. This laminate can then be allowed to relax and will return to about the original 100 mm, but with 250 mm of nonwoven. There can be more than one installed elongation within one waistband laminate if the elastics are strained to a different degree. For example, strand (1) is stretched from 100 mm to 250 mm when combined with the nonwoven or has 150% installed elongation while strand (2) is stretched from 90 mm to 250 mm when combined with the NW or has an installed elongation of about 178%.

The Applied Waistband Strain is the strain that the waistband laminate is under when combined with the absorbent article. For example if 100 mm of laminate is stretched to 170 mm when applied it would be considered to be 70% applied waistband strain or $((170 \text{ mm}-100 \text{ mm})/100 \text{ mm} \times 100\%)$. In one embodiment, the first installed elongation of any number of elastic strands is about 100%, about 125%, about 140%, about 150%, about 160%, about 175%, about 200%. In one embodiment the second installed elongation of any number of elastic strands is about 100%, about 125%, about 140%, about 150%, about 160%, about 175%, about 200%.

In one embodiment, the delta between the first installed elongation and the second installed elongation is greater than about 20%, greater than about 30%, greater than about 40%.

In one embodiment, the resulting Front-to-Back Delta Chassis Contraction is greater than about 5.0%, greater than about 9.0%, greater than about 9.5%, greater than about 12.5%, greater than about 15%, greater than about 20%.

In one embodiment, the Front-to-Back Delta Chassis Contraction is less than about 15%, less than about 12.5%, less than about 10%, less than about 9.5%, less than about 9% when either the front chassis contraction or the back chassis contraction is greater than about 18%, greater than about 20%.

Figure 9A:
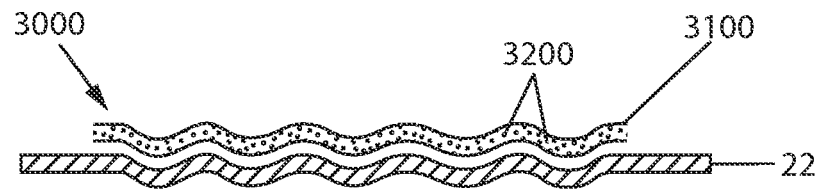
FIGS. 9a-d are schematic cross section views of embodiments of waistband laminates suitable for use in the absorbent articles detailed herein.
Figure 9B:
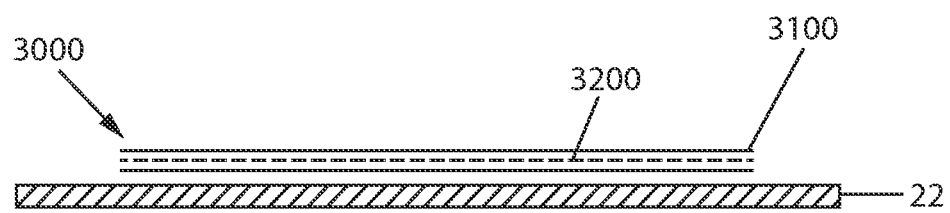
Figure 9C:
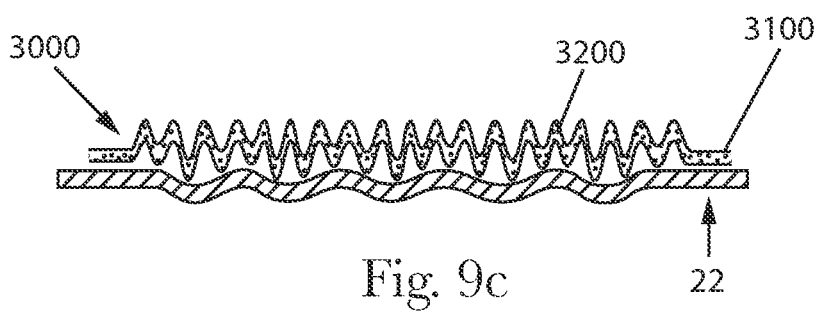
Figure 9D:
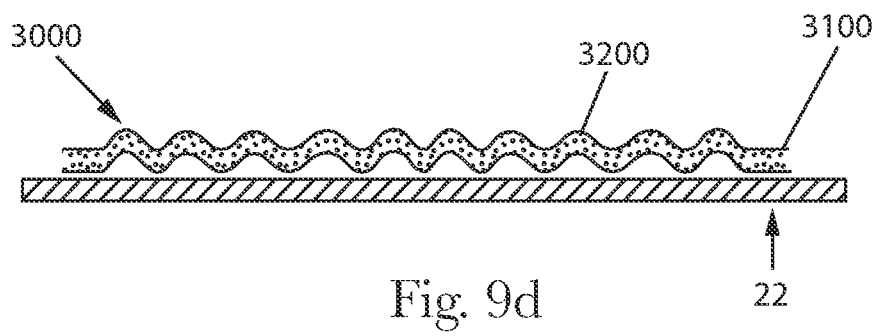

Another object of the disposable absorbent articles detailed herein is to deliver a better balance of thickness (caliper)/cushion and contraction in a waistband than what is currently known in the art. Presently, most waistbands are either foam based which have good cushion/caliper for comfort and containment but are limited in the amount of contraction or the waistbands are a combination of elastic strands and nonwoven where the elastic strands are pulled at high strain which delivers high contraction, but very little caliper/cushion in use. Thus, one embodiment of the disposable absorbent articles detailed herein is directed to "consolidation" which provides a waistband having the nonwoven material and the elastic strand(s) combined under a higher first strain (installed elongation) and the resulting waistband attached to the article under a lower applied waistband strain, such that the folded up nonwoven in the waistband provides a cushion/caliper in both the relaxed and stretched/in use states. FIG. 9 depicts cross sectional views of the waistband laminate (3000). FIGS. 9a-b depict cross sections of the waistband with no extended consolidation. FIG. 9a depicts a relaxed product cross section at the waist, parallel to the lateral axis of the diaper chassis (22). FIG. 9b shows an extended product cross section at the waist, parallel to the lateral axis of the diaper. FIGS. 9c-d depict cross sections of the waistband with extended consolidation. FIG. 9c shows a relaxed product cross section at the waist, parallel to the lateral axis of the diaper. FIG. 9c shows that the frequency and amplitude of the waistband is higher than that of the chassis it is applied to. FIG. 9d shows an extended product cross section at the waist, parallel to the lateral axis of the diaper. FIG. 9d shows that even when the chassis is extended, the waistband still has gathers and caliper.

In one embodiment, the waistband is comprised of a laminate comprising a nonwoven material and at least one elastic strand, wherein the nonwoven material and the elastic strand(s) are combined under a first strain and the waistband is attached to the article under an applied waistband strain. In one embodiment, the first strain, also referred to as the installed strand elongation, is greater than about 50%, greater than about 75%, greater than about 100%, greater than about 150%, greater than about 200%, greater than about 225%, greater than about 250%, greater than about 300%, greater than about 350%, greater than about 375%. In one embodiment, the applied waistband strain, also referred to as the waistband strain is greater than about 25%, greater than about 50%, greater than about 75%, greater than about 100%. In one embodiment, the difference between the first strain and the applied waistband strain, also referred to as Consolidation, is greater than about 0%, greater than about 65%, greater than about 75%, greater than about 100%, greater than about 150%, greater than about 200%, greater than about 225%, greater than about 250%, greater than about 300%.

In one embodiment, the waistband has a Full Waistband Consolidation greater than about 95%, greater than about 100%, greater than about 125%, greater than about 150%, greater than about 175%, greater than about 200%.

In one embodiment, the waistband had an Extended Waistband Consolidation greater than about 35%, greater than about 50%, greater than about 75%, greater than about 100%, greater than about 125%, greater than about 175%.

In one embodiment, the waistband is attached near the waist edge. In one embodiment, the waistband is attached within 20 mm of the waist edge. In one embodiment, the waistband is attached flush with the waist edge (i.e., the waistband is coterminous with the waist edge). In one embodiment, the waistband is present only at one waist edge. In one embodiment, the waistband is present at both the first and second waistband edges.

The nonwoven material and the elastic strand(s) may be combined with adhesive, mechanical bonds, or any other forms of attachment known in the art. The waistband may be attached to the article with adhesive, mechanical bonds, or any other forms of attachment known in the art.

In one embodiment, the relaxed caliper of the waistband is greater than about 1.60 mm, greater than about 2.00 mm, greater than about 2.25 mm, greater than about 2.50 mm.

In one embodiment, the extended caliper of the waistband is greater than about 0.80 mm, greater than about 1.00 mm, greater than about 1.25 mm.

Another object of the open form disposable absorbent articles detailed herein is to include a first waist region 36 with a stretchable front waist feature (e.g., first waistband 1000), wherein the first waist region 36 is flexible and comfortable to wear, promotes continuous contact with the wearer's body, and resists rolling, flipping or scrunching. Further, if the first waist region 36 of the open form disposable absorbent articles detailed herein does roll, flip or scrunch, the first waist region 36 has a tendency to return to its original position in contact with the wearer's body.

As explained in the Background section above, previous known open form disposable absorbent articles sometimes employ materials with a high stiffness in the front waist region in order to counteract the bending and buckling forces exerted by a wearer's body. However, the increased stiffness results in a front waist region which does not conform to the body of the wearer as the body changes shape during use due to a wearer's posture, breathing, food intake, etc., and therefore is uncomfortable for the wearer. Accordingly, in addition to promoting continuous contact with a wearer's body, the front waist assembly of the open form disposable absorbent articles detailed herein may also have a low stiffness to promote comfort for the wearer.

Materials deform (e.g., bend, buckle) when sufficient force is applied, and the higher this force the more stiff a material is considered. Some materials undergo permanent or semi-permanent deformation when the force applied to them exceeds their stiffness. Other materials reversibly deform under a particular range of forces, and will attempt to return to their original shape when the force is released (e.g., a spring). The energy that a material is able to utilize when returning to its original shape is defined as the material's resiliency. Accordingly, a material that has a relatively low stiffness and relatively high resiliency is desirable for utilization in a first waist region 36 of an open form disposable absorbent article 20. In creating first waist regions 36 which promote continuous contact with a wearer's body and resist rolling, flipping and/or scrunching, the first waist region may have a resiliency that is greater than about 5 mJ, greater than about 5.5 mJ, greater than about 6.0 mJ, greater than about 6.1 mJ, greater than about 6.2 mJ, greater than about 6.3 mJ, greater than about 6.4 mJ, greater than about 6.5 mJ, greater than about 7.0 mJ, greater than about 7.5 mJ, greater than about 8.0 mJ, greater than about 8.5 mJ, greater than about 9.0 mJ, greater than about 9.5 mJ, greater than about 10.0 mJ, greater than about 10.5 mJ, greater than about 11.0 mJ, greater than about 11.5 mJ, greater than about 12.0 mJ, greater than about 12.5 mJ, greater than about 13.0 mJ, greater than about 13.5 mJ, greater than about 14.0 mJ, greater than about 14.5 mJ, or greater than about 15.0 mJ; and a stiffness of less than about 11.0 N, less than about 10.0 N, less than about 9.0 N, less than about 8.0 N, less than about 7.0 N, less than about 6.0 N, less than about 5.0 N, or less than about 4.0 N. In some embodiments, it may be desirable for the first waist region to have a resiliency of between about 5.0 mJ and about 15.0 mJ, or between about 5.0 mJ and about 10.0 mJ. In some embodiments, it may be desirable for the first waist region to have a stiffness of between about 4.0 N and 10.0 N, or between about 6.0 N and about 10.0 N. In some embodiments, it may be desirable for the first waist region to have a resiliency of greater than about 5.0 mJ and a stiffness of less than about 10.0 N. The resiliency and stiffness parameters are measured in the first waist region as defined below in the Test Methods section. In order to calculate the resiliency and stiffness of the first waist region 36, the open form disposable absorbent article 20 is tested with a marked location 322 that is 15 mm inboard of the waist edge 14 of the first waist region 36. Thus, the resiliency and stiffness testing procedure is run according to the First Waist Region Stiffness and First Waist Region Resiliency Method detailed below, with 15 mm of the first waist region 36 hanging over the test edge 318 of the test surface 311 of the support platform 310.

In creating waist features which do not roll, flip and/or scrunch, it may also be helpful to eliminate areas within the front waist of the product where the resiliency falls substantially below the resiliency of the surrounding areas. The first waist region 36 may include nine sections that run parallel to the waist edge 14 of the disposable absorbent article. As illustrated in FIG. 11, within the first waist region 36, the disposable absorbent articles detailed herein may include a first section 1, a second section 2, a third section 3, a fourth section 4, a fifth section 5, a sixth section 6, a seventh section 7, an eighth section 8, and a ninth section 9. The first section is 10 mm in width, and each section after that is 5 mm in width. Accordingly, the first section 1 of first waist region 36 is the area between waist edge 14 and a line 101 that is parallel to waist edge 14 that is 10 mm inboard of waist edge 14. The second section 2 of first waist region 36 is the area between the line 101 that is parallel to waist edge 14 that is 10 mm inboard of waist edge 14, and a line 102 that is parallel to waist edge 14 that is 15 mm inboard of waist edge 14. The third section 3 of first waist region 36 is the area between the line 102 that is parallel to waist edge 14 that is 15 mm inboard of waist edge 14, and a line 103 that is parallel to waist edge 14 that is 20 mm inboard of waist edge 14. The fourth section 4 of first waist region 36 is the area between the line 103 that is parallel to waist edge 14 that is 20 mm inboard of waist edge 14, and a line 104 that is parallel to waist edge 14 that is 25 mm inboard of waist edge 14. The fifth section 5 of first waist region 36 is the area between the line 104 that is parallel to waist edge 14 that is 25 mm inboard of waist edge 14, and a line 105 that is parallel to waist edge 14 that is 30 mm inboard of waist edge 14. The sixth section 6 of first waist region 36 is the area between the line 105 that is parallel to waist edge 14 that is 30 mm inboard of waist edge 14, and a line 106 that is parallel to waist edge 14 that is 35 mm inboard of waist edge 14. The seventh section 7 of first waist region 36 is the area between the line 106 that is parallel to waist edge 14 that is 35 mm inboard of waist edge 14, and a line 107 that is parallel to waist edge 14 that is 40 mm inboard of waist edge 14. The eighth section 8 of first waist region 36 is the area between the line 107 that is parallel to waist edge 14 that is 40 mm inboard of waist edge 14, and a line 108 that is parallel to waist edge 14 that is 45 mm inboard of waist edge 14. The ninth section 9 of first waist region 36 is the area between the line 108 that is parallel to waist edge 14 that is 45 mm inboard of waist edge 14, and a line 109 that is parallel to waist edge 14 that is 50 mm inboard of waist edge 14.

In certain embodiments, the difference in resiliency between two adjacent sections 1, 2, 3, 4, 5, 6, 7, 8, 9 is not more than about 60% of the average resiliency of all the sections 1, 2, 3, 4, 5, 6, 7, 8, 9, in the first waist region 36. Shown as a calculation: Δ Resiliency between adjacent sections=(Absolute Value of (Resiliency of a section−Resiliency of an adjacent section))/Resiliency average for all sections ≤60%. In other embodiments, the difference in resiliency between two adjacent sections 1, 2, 3, 4, 5, 6, 7, 8, 9 is not more than about 40%, about 45%, about 50%, about 65%, about 70%, about 80%, about 90%, or about 100% of the average resiliency of all the sections 1, 2, 3, 4, 5, 6, 7, 8, 9, in the first waist region 36. In addition to the difference in resiliency between two adjacent sections of the first waist region 36, some embodiments of open form disposable absorbent product 20 also include a first waist region 36 stiffness of less than about 11.0 N, less than about 10.0 N, less than about 9.0 N, less than about 8.0 N, less than about 7.0 N, less than about 6.0 N, less than about 5.0 N, or less than about 4.0 N. Such stiffness is measured 15 mm inboard of the waist edge 14 of the first waist region 36 (i.e., at line 102 that separates section 2 from section 3). The resiliency parameters specific to each section of first waist region 36 are measured as defined below in the Test Methods section. In order to calculate the resiliency of the first section 1, the open form disposable absorbent article 20 is tested with a marked location 322 that is 10 mm inboard of the waist edge 14 of the first waist region 36. Accordingly, the resiliency and stiffness testing procedure is run according to the First Waist Region Stiffness and First Waist Region Resiliency Method detailed below, with 10 mm of the first waist region 36 hanging over the test edge 318 of the test surface 311 of the support platform 310. In order to calculate the resiliency of the second section 2, the open form disposable absorbent article 20 is tested with a marked location 322 that is 15 mm inboard of the waist edge 14 of the first waist region 36. The testing of each subsequent section follows accordingly (third section 3 is tested with a marked location 322 that is 20 mm inboard of the waist edge, fourth section 4 is tested with a marked location that is 25 mm inboard of the waist edge, etc.).

Resiliency and stiffness are material properties that can change based on the physical configuration or structure of a material as well as the composition of the material One embodiment of the open form disposable absorbent articles detailed herein includes a non-woven material which gains resiliency through its three-dimensional structure. Corrugating the non-woven material may provide this three dimensional structure. Additionally, the following structural elements are believed to impact resiliency in nonwoven materials: thickness, density, basis weight, uniformity and/or regularity in the corrugations, fibers which are curled (e.g., bi-component fibers which are curled), differential strain lamination, mechanical properties of the polymer, and the material's ability to non-plastically deform under strain.

As shown in FIG. 1, if the waistband is 25 mm or greater in the longitudinal direction, the waist assembly 35 is the area of first waist region 36 that is between waist edge 14 and a line 201 that is parallel to waist edge 14 that is 25 mm inboard of waist edge 14. If the waistband is shorter than 25 mm in the longitudinal direction, the waist assembly 35 is defined as the area of the first waist region that is between the waist edge 14 and the inboard edge of the waistband.

Without being bound by theory, when a waist assembly 35 of the first waist region 36 of an open form disposable absorbent article is bent away from the wearer's body, the body-facing surface of the waist assembly 35 attempts to travel over a longer path when compared to the garment-facing surface, due to the radius of curvature being longer for the body facing surfaced. The longer path of travel is due to the thickness of the materials comprising the waist assembly 35. Having corrugations in the waist assembly 35 can increase its effective thickness. Accordingly, the body-facing surface of the waist assembly 35 is placed in tension. Thicker materials in the waist assembly 35 (e.g., higher basis weight) and/or deeper the corrugations lead to more tension in the body-facing surface of the material. This tension causes the waist assembly 35 to have a propensity to return to its original shape. Regular and consistent corrugations cause even more tension because such corrugations are more energetically stable. Conversely, irregular corrugations may indicate that the waist region 35 has natural weak points or spots where tension stored in a waistband can be relieved. Reliving the tension stored in the waist assembly 35 may reduce the energy available to return it to its upright state. In addition, the resiliency of the waist assembly 35 may be increased through waistband consolidation, as further detailed herein.

Further, curled fibers may act as tiny springs in the material of the waist assembly 35. As the waist assembly 35 bends, the springs on the body-facing surface extend, and the springs on the garment facing surface are compressed. This compression/tension may return the material to its original shape. In addition, differential strain may cause the waist assembly 35 to bend in a particular direction (i.e., towards the body) in order to relax the higher strain in the body facing surface. As the waist assembly 35 is bent away from the body, the body facing surface is put under incrementally more strain than an equivalent surface which was laminated at equal strain.

Figure 12A:
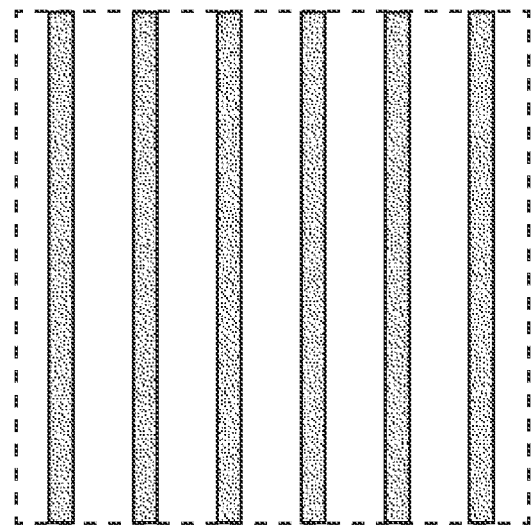
FIG. 12 A-D illustrate an embodiment of a non-woven with a deep continuous bond pattern that can be elastically gathered to include regular and consistent corrugations.
Figure 12B:
Figure 12C:
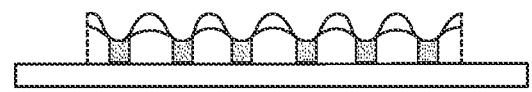
Figure 12D:
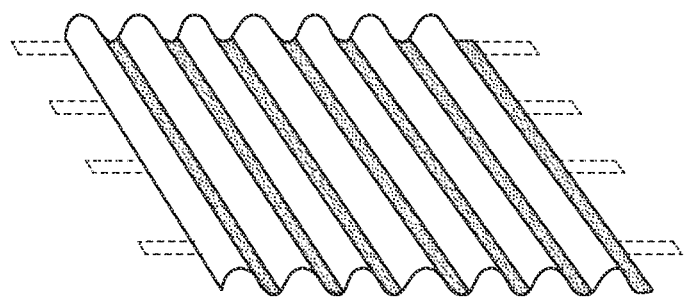
Figure 13A:
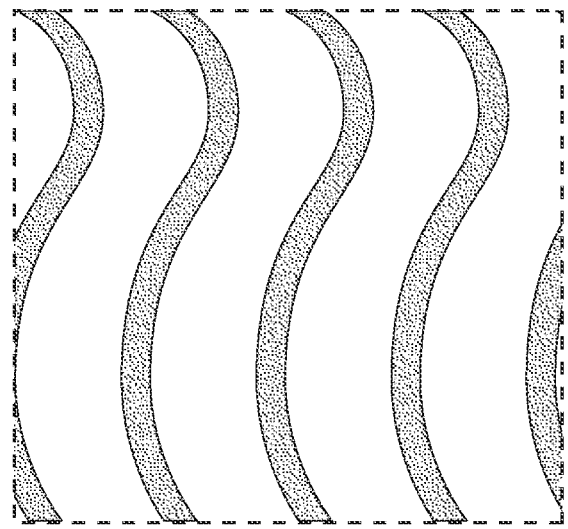
FIG. 13 A-D illustrate an embodiment of a non-woven with a deep continuous bond pattern that can be elastically gathered to include regular and consistent corrugations.
Figure 13B:
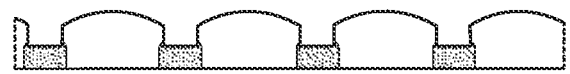
Figure 13C:
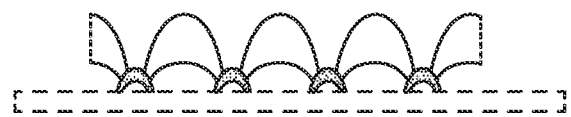
Figure 13D:
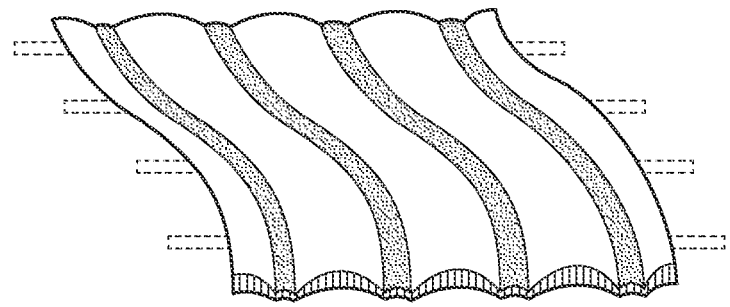

Corrugations are often difficult to create in inexpensive non-woven materials. One method for creating such corrugations is to use a deep bond pattern in a relatively thick non-woven such that the bond pattern creates columns in the longitudinal direction waist assembly 35 of the absorbent article. When such a non-woven is consolidated in the lateral direction, the bond sites will tend to buckle while the unbonded sites will tend to pucker up, creating corrugations. If the bonds are created in a regular pattern, the corrugations will also tend to be regular. FIGS. 12A-D and 13A-D illustrate two non-limiting examples of non-woven with a deep continuous bond pattern that can be employed in waist assembly 35 and that include regular and uniform corrugations. FIG. 12 illustrates a regular straight bond pattern in the flat nonwoven as show in FIG. 12A, and FIG. 13 illustrates a regular wavy bond pattern in the flat nonwoven as shown in FIG. 13A. FIGS. 12B and 13B illustrate cross sectional profiles of the bond patterns in the flat nonwovens of FIGS. 12A and 13A. FIGS. 12C and 13C illustrate the cross sectional profiles of the bond patterns when the nonwovens are elastically contracted, thus forming regular corrugations. FIGS. 12D and 13D illustrate perspective views of the of the bond patterns when the nonwovens are elastically contracted, thus forming regular corrugations. Other bond patterns are also contemplated, as long as the bond patterns are consistent and travel substantially the continuous longitudinal dimension of the waistband material Additional bond patterns may include zigzag bond lines, diagonal bond lines, or any other pattern where a line drawn laterally across the waistband does not intersect any single bond line more than once. As used herein, the term "bond line" refers to a plurality of sites on a substrate where the fibers of the substrate have been joined together. Joining can be accomplished through various means such as thermal bonds, pressure bonds, ultrasonic welds, glue bonds, or the like. The plurality of sites can be joined together to form the "line". However, the term "line", as used herein, can also describe a series of discrete points or short lines closely spaced so as to effectively approximate a line. Therefore, those skilled in art will recognize that although a solid line bonding pattern is described, the benefits of the present invention can similarly be achieved by closely spaced points or discrete line segments which effectively approximate a line.

Figure 14:
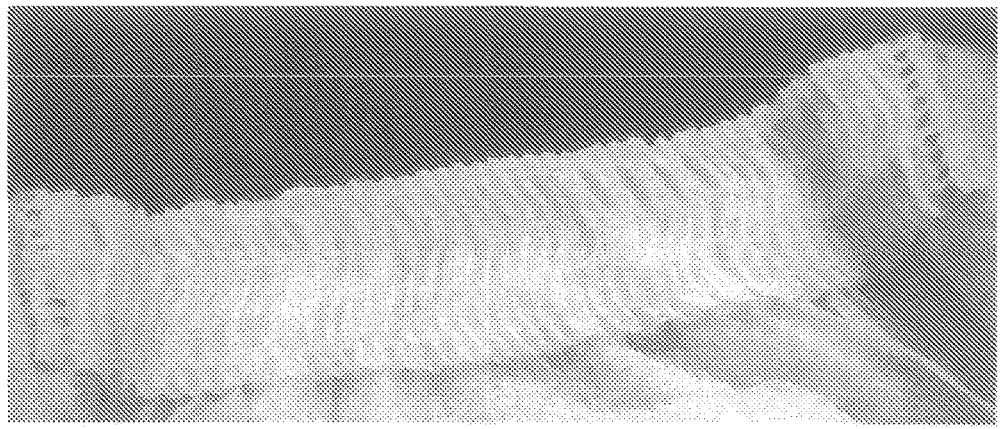
FIG. 14 is a photograph of an embodiment of a waistband suitable for use in the open form disposable absorbent articles detailed herein.
Figure 15:
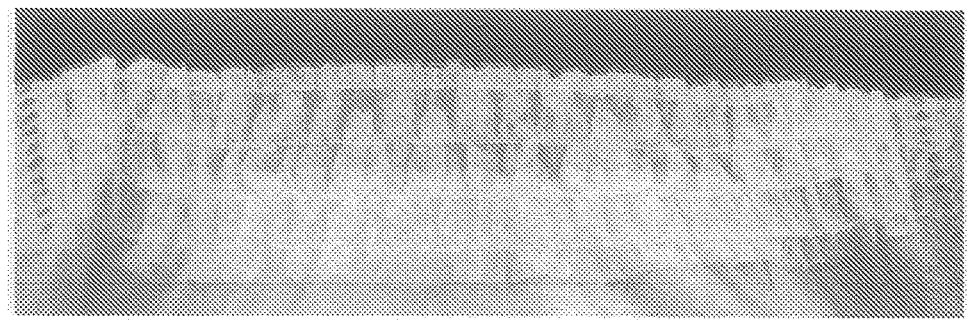
FIG. 15 is a photograph of a waistband without regular and uniform corrugations.
Figure 16:
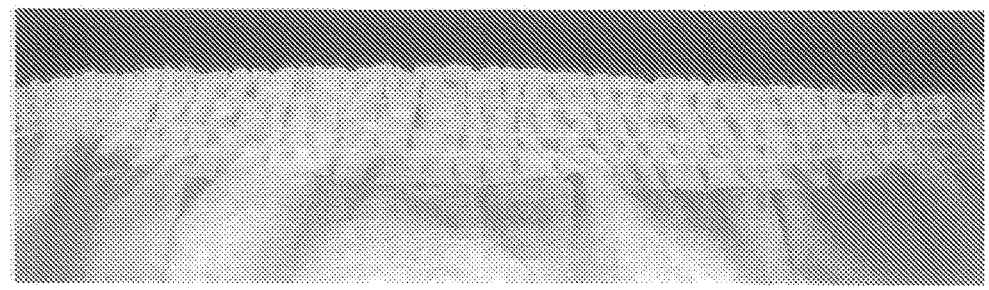
FIG. 16 is a photograph of a waistband without regular and uniform corrugations.

FIG. 14 is a photograph of a waist assembly that contains regular and uniform gathers. The waistband of FIG. 14 was constructed from a 30 gsm side-by-side bi-component polyethylene/polypropylene non-woven with a wavy bond pattern (the details of the pattern can be found in US2010298796). The bond in the bond pattern is about 1 mm wide, the unbonded region is about 2.5 mm wide, the wave amplitude is about 4 mm, and the wave frequency is about 0.04 $mm^{-1}$. The elastic installed elongation is 90%, and the applied waistband strain is 11%. FIG. 15 is a photograph of a waist assembly that contains irregular gathers. The waistband of FIG. 15 was constructed from a 15 gsm side-by-side bi-component polyethylene/polypropylene non-woven with a wavy bond pattern (the details of the pattern can be found in US2010298796). The bond in the bond pattern is about 1 mm wide, the unbonded region is about 2.5 mm wide, the wave amplitude is about 4 mm, and the wave frequency is about 0.04 $mm^{-1}$. The elastic installed elongation is 90%, and the applied waistband strain is 11%. FIG. 16 is a photograph of a waist assembly that contains irregular gathers. The waistband of FIG. 16 was constructed from a 10 gsm SMS non-woven with a bond pattern consisting of small dots. The elastic installed elongation is 90%, and the applied waistband strain is 11%. All waistband adhesives are spiral glue.

More regular and consistent/uniform corrugations potentially yield more resiliency to the waist assembly 35 of the first waist region 36. To create more consistent corrugations, it may be advantageous to match the frequency of the bond sites, the stiffness of the non-bonded material, and the desired amount of installed elongation. As one non-limiting example, if the desired installed elongation level may be about 60% to about 150% and the non-woven basis weight may be about 20 gsm to about 75 gsm, a bond frequency of about 0.1 $mm^{-1}$ to about 2.0 $mm^{-1}$ may be desirable. In other examples of the waist assembly 35 of the open form disposable absorbent articles 20 detailed herein, the desired installed elongation level may be about 75% to about 115%, or about 80% to about 100%; the non-woven basis weight may be about 20 gsm to about 50 gsm, or about 25 gsm to about 45 gsm, or about 25 gsm to about 35 gsm, or about 30 gsm; and a bond frequency may be about 0.1 $mm^{-1}$ to about 1.5 $mm^{-1}$, or about 0.1 $mm^{-1}$ to about 1.0 $mm^{-1}$, or about 0.1 $mm^{-1}$ to about 0.75 $mm^{-1}$. In one particular embodiment, the waist assembly 35 may include a waistband that has an elastic installed elongation of about 90%, a non-woven basis weight of about 30 gsm, and a bond frequency of about 0.5 $mm^1$.

Further, it may also be important that such corrugations are present when the product is configured to be worn. Many waistbands which may appear corrugated in a relaxed state are actually laminated flat against the diaper chassis, thus there are no corrugations when the front of the diaper is stretched when being worn. Consolidating the waistband (as described herein) prior to application to waist band assembly 35 is one means to ensure that corrugations are still present when the diaper is configured to be worn.

Another method for creating regular corrugations is to use glue or other attachment means which create discretely spaced columns in the longitudinal direction of the absorbent article. These attachment means can be used internally to assemble components of the stretch feature (e.g., to attach elastic strands to a non-woven material), or to attach the stretch feature to another part of the absorbent article. This method can also be used to create uniform gathers which run the entire longitudinal length of the waistband assembly 35.

Regular corrugations are corrugations which are substantially evenly spaced and sized. This helps ensure that forces are distributed evenly across the waist assembly 35. Also, since nonwovens are typically made in large webs with substantially regular properties across the web, and since the corrugation size is dependent on the stiffness of this web, creating regular corrugations prevents any particular corrugation from having sub-optimal strength by being differently sized than its neighbors. Uniform corrugations are corrugations which are continuous from the waist edge 14 of the first waist region 36 to the bottom of the waist assembly 35 without being broken, disrupted, or forked. Breaks, disruptions, and forks may indicate weak spots in the corrugation structure.

In creating waist features which do not roll, flip and/or scrunch, it may also be helpful to eliminate areas that allow hinge lines to form across the front waist region 36, i.e., where bending is likely to occur. Hinge lines can be created where materials have significantly lower bending strengths than the surrounding areas. Eliminating hinge lines can be accomplished by adding significant stiffness to all the areas in the first waist region 36, but this can result in a first waist region that is stiff enough to cause discomfort to the wearer. Hinge lines can typically also occur at the lateral edge of a material or component which is a portion of the first waist region 36. An example of this is at the bottom edge of the waistband in the first waist region 36, or at the top edge of the absorbent assembly in the first waist region 36. Another area where a hinge line can occur is at the top or bottom edges of the fastening system, particularly in systems with rectangular shaped fastening elements. The area where a given material ends (e.g., the lateral waistband edge) usually corresponds to an area of thickness change of the first waist region 36. Without being bound by theory, thickness is a key variable in the flexibility of materials, and an area where there is a significant thickness change can result in a significant flexibility difference versus the adjacent areas. Therefore it is desirable to create smooth flexibility transitions between material edges that are less abrupt, to spread the change in flexibility over a wider area. This can be accomplished effectively by ensuring there is sufficient overlap between the edges of materials, and avoiding components that co-terminate or have slight gaps.

Figure 19:
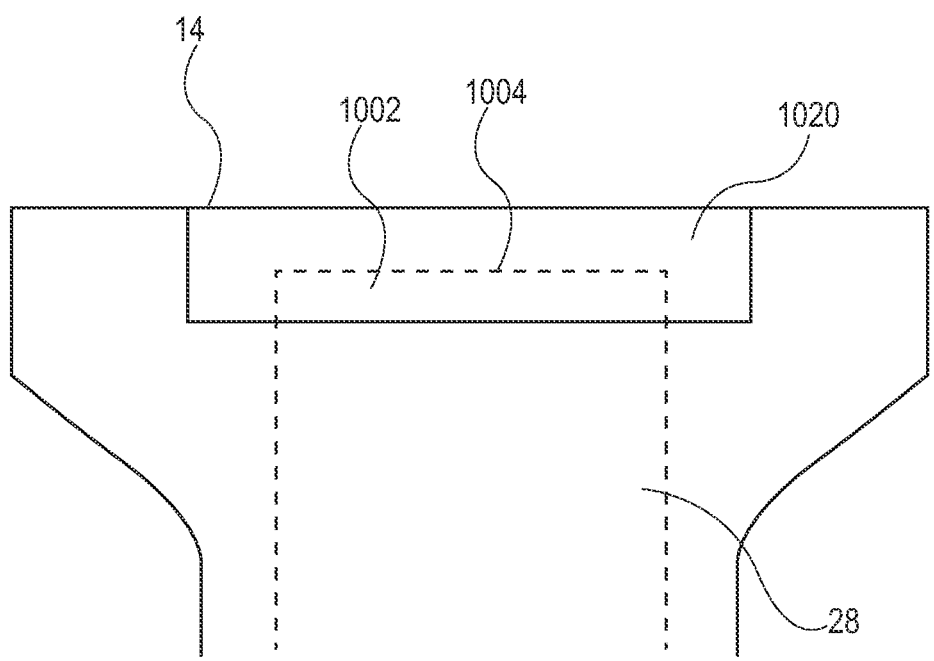
FIG. 19 is a schematic representation of a top view of the body facing surface of an exemplary open form disposable absorbent article.

In one embodiment, the open form disposable absorbent articles detailed herein include a first waist region, a second waist region, a crotch region disposed between the first waist region and second waist region; a first waist edge and a second waist edge; at least one fastener in the second waist region; and at least one waistband in the first waist region adjacent the first waist edge; a topsheet, a backsheet, and an absorbent core disposed between the top sheet and backsheet; wherein the first waist region contains an overlap between the absorbent core and the waistband. FIG. 19 shows a garment facing surface of an exemplary open form disposable absorbent article as disclosed herein. In FIG. 19, the waistband 1000 in the first waist region overlaps with absorbent core 28 to form an overlap region 1002. As previously detailed, the absorbent core 28 may comprise a core cover, a dusting layer, and a wide variety of liquid-absorbent materials commonly used in disposable diapers and other absorbent articles. In the illustrated embodiment, the lateral edge 1004 of the absorbent core 28 is inboard of the waist edge 14 of the first waist region 26. The overlap region 1002 may create a smoother transition between the edge of the waistband 1000 and the edge of the absorbent core 28, therefore spreading the change in flexibility over a wider area and reducing bending/buckling occurrences.

In one non-limiting embodiment, the waistband extends 26 mm from the first waist edge, and the absorbent core is spaced 14 mm from the first waist edge, creating a 12 mm overlap region in the longitudinal direction between the waistband and the absorbent core. In some embodiments, the overlap region ranges in the longitudinal direction from about 5 mm to about 25 mm, or from about 7.5 mm to about 20 mm, or from about 10 mm to about 15 mm. In some embodiments, overlap regions can be about 2 mm, about 4 mm, about 6 mm, about 8 mm, about 10 mm, about 12 mm, about 14 mm, about 16 mm, about 18 mm, about 20 mm, about 22 mm, about 24 mm, about 26 mm, about 28 mm or about 30 mm.

Figure 17:
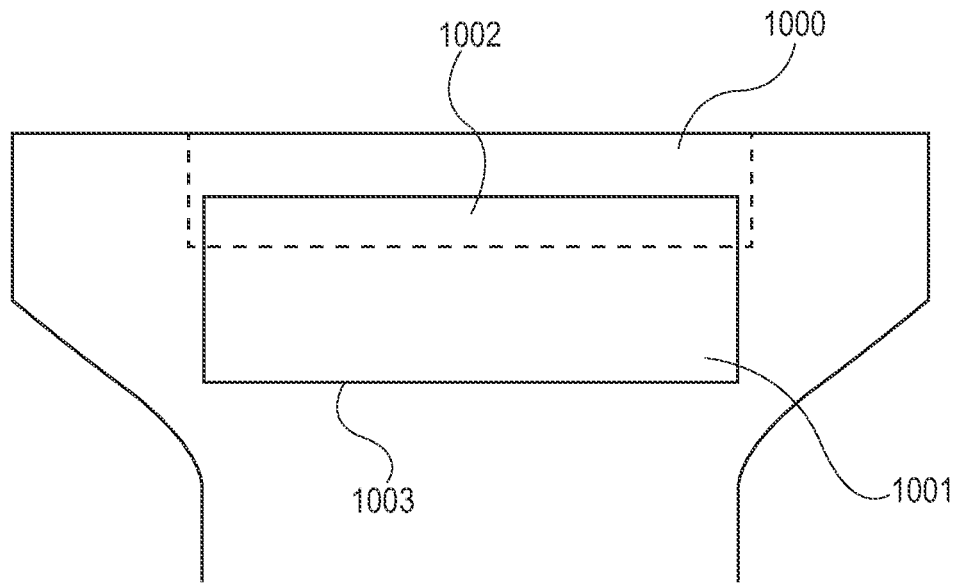
FIG. 17 is a schematic representation of a top view of the garment facing surface of an exemplary open form disposable absorbent article.
Figure 18:
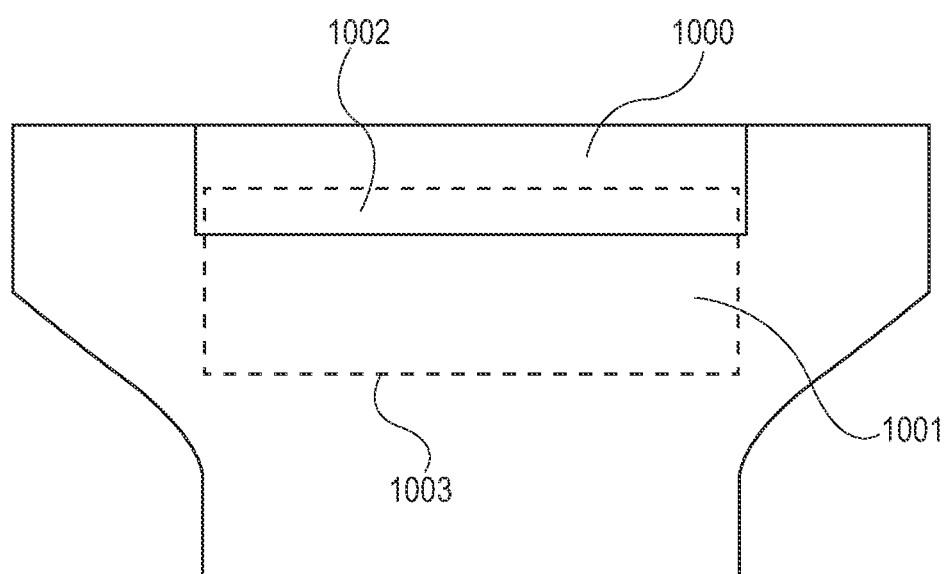
FIG. 18 is a schematic representation of a top view of the body facing surface of an exemplary open form disposable absorbent article.

In another embodiment, the open form disposable absorbent articles detailed herein include a first waist region, a second waist region, a crotch region disposed between the first waist region and second waist region; a first waist edge and a second waist edge; at least one fastener in the second waist region; at least one discrete landing zone in the first waist region; and at least one waistband in the first waist region adjacent the first waist edge; wherein the first waist region contains an overlap between the discrete landing zone and the waistband. FIG. 18 shows a body facing surface of an exemplary open form disposable absorbent article as disclosed herein. FIG. 17 shows a garment facing surface of an exemplary open form disposable absorbent article as disclosed herein. In FIG. 17, the waistband 1000 in the first waist region overlaps with discrete landing zone 1001 to form an overlap region 1002. In this illustrated embodiment, the lateral inboard edge 1003 of discrete landing zone 1001 is not overlapped with the waistband 1000. The overlap region 1002 may create a smoother transition between the edge of the waistband 1000 and the edge of the discrete landing zone 1001, therefore spreading the change in bending strength over a wider area and reducing bending/buckling occurrences.

In one non-limiting embodiment, the waistband extends 26 mm from the first waist edge, and the discrete landing zone is spaced 14 mm from the first waist edge, thus creating a 12 mm overlap region in the longitudinal direction between the waistband and discrete landing zone. In some embodiments, the overlap region ranges in the longitudinal direction from about 5 mm to about 25 mm, or from about 7.5 mm to about 20 mm, or from about 10 mm to about 15 mm. In some embodiments, overlap regions can be about 2 mm, about 4 mm, about 6 mm, about 8 mm, about 10 mm, about 12 mm, about 14 mm, about 16 mm, about 18 mm, about 20 mm, about 22 mm, about 24 mm, about 26 mm, about 28 mm or about 30 mm.

Another object of the disposable absorbent articles detailed herein is to deliver an integrated leg gasketing system and front/back waistband feature that provides extra leakage protection around the perimeter of the article. Thus, one embodiment of the disposable absorbent articles detailed herein is directed to "360 Leakage Protection"

which provides a common leg gasketing system and waistband with similar construction having similar gather counts. Additional embodiments may include leg gasketing systems and waistbands that overlap or have similar tints, textures, bond patterns, colors, or other visual cues. FIG. 3 depicts an embodiment having gathers in both the waist assemblies and leg gasketing system.

In one embodiment, the waistband overlaps the leg gasketing system in the first waist region. In one embodiment, the waistband overlaps the leg gasketing system in the second waist region. In one embodiment, the waistband overlaps the leg gasketing system in both the first waist region and the second waist region. In one embodiment, the waistband laterally terminates within the span of the leg gasketing system in the first waist region, thus partially overlapping the leg gasketing system in the first waist region. In one embodiment, the waistband laterally terminates within the span of the leg gasketing system in the second waist region, thus partially overlapping the leg gasketing system in the second waist region. In one embodiment, the waistband laterally terminates within the span of the leg gasketing system in the first waist region and the second waist region, thus partially overlapping the leg gasketing system in the first waist region and the second waist region.

In one embodiment, the disposable absorbent article comprises a waistband and a leg gasketing system, as described herein, wherein the leg gasketing system has a first gather count and the waistband has a second gather count such that the ratio of the first gather count to the second gather count is greater than about 0.5, greater than about 0.75, less than about 1.25, less than about 1.50. In one embodiment, the ratio of the first gather count to the second gather count is about 1.00. In one embodiment, the ratio of the first gather count to the second gather count is from about 0.75 to about 1.25. In one embodiment, the ratio of the first gather count to the second gather count is from about 0.75 to about 1.25, when the leg gasketing system gather count is greater than about 13. In one embodiment, the ratio of the first gather count to the second gather count is from about 0.75 to about 1.25, when the waistband gather count is greater than about 12. In one embodiment, the ratio of the first gather count to the second gather count is from about 0.75 to about 1.25, when the absorbent article is a taped-type product.

In one embodiment, both of the waistband and leg gasketing system comprise elastic strands; in one embodiment, the waistband comprises elastic strands; in one embodiment, both the waistband and leg gasketing system comprise the same type of stretch material and/or laminate structure.

In one embodiment, the waistband has greater than about 10 gathers per 30 mm section, greater than about 12 gathers per 30 mm section. In one embodiment, the leg gasketing system has greater than about 10 gathers per 30 mm section, greater than about 12 gathers per 30 mm section.

In one embodiment, the waistband is present in the first waist edge and the second waist edge and the leg gasketing system is present in the first longitudinal edge and the second longitudinal edge.

The absorbent article 20 may include a leg gasketing system 70 as described in U.S. Patent Publication Nos. US 2012/0277713A1 and US 2012/0277702A1, both filed on Apr. 29, 2011. FIGS. 4 and 5 depict schematic cross section views of exemplary leg gasketing systems. The leg gasketing system 70 may comprise an inner barrier leg cuff 71 comprising an inner cuff folded edge 72 and an inner cuff material edge 73. The leg gasketing system 70 may further comprise an outer cuff 74 comprising an outer cuff folded edge 75 and an outer cuff material edge 76.

In one embodiment, the leg gasketing system 70 comprises one web of material. An embodiment having one web of material may provide a cost advantage over embodiments having more than one web of material. Further, an embodiment having one web of material may have fewer leaks, as there are no holes created by bonding more than one web of material. Also, an embodiment having one web of material may be more aesthetically pleasing, as few mechanical bonds are visible.

In one embodiment, the leg gasketing system 70 has an inner barrier leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. In one embodiment, the web of material is folded laterally inward to form the outer cuff folded edge 75 and folded laterally outward to form the inner cuff folded edge 72. In one embodiment, the leg gasketing system 70 extends from the first waist edge 36 to the second waist edge 38 and is joined to the topsheet 24 and/or backsheet 26 between the inner cuff folded edge 72 and the outer cuff folded edge 75 in the crotch region 37. In one embodiment, the outer cuff material edge 76 is disposed laterally inboard the inner cuff material edge 73.

In one embodiment, the outer leg cuff 74 comprises elastic members 77 positioned in a lateral array between the outer cuff folded edge 75 and outer cuff material edge 76; the outer leg cuff 74 optionally comprises at least two elastic members 77, at least three elastic member 77, at least four elastic members 77, at least five elastic members 77, at least six elastic members 77. In one embodiment, the elastic members 77 may be disposed between the outer cuff folded edge 75 and the inner cuff material edge 73.

In one embodiment, the inner barrier leg cuff 71 comprises an array of elastic members 78 in the area of the inner cuff folded edge 72; the inner barrier leg cuff 71 optionally comprises at least one elastic member 78, at least two elastic members 78, at least three elastic members 78, at least four elastic members 78, at least five elastic members 78. In one embodiment, the elastic members 78 may be disposed between the inner cuff folded edge 72 and the outer cuff material edge 76.

In one embodiment, the leg gasketing system 70 has an inner barrier leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. The leg gasketing system may comprise a first material comprising the inner barrier leg cuff 71 and a second material comprising the outer cuff 74. The first and second material may overlap and be joined together along a longitudinal edge of each material by any suitable bonding means. In one embodiment, the web of material is folded laterally inward to form the outer cuff folded edge 75 and folded laterally outward to form the inner cuff folded edge 72. In one embodiment, the proximal edges of the outer cuff 74 are coterminous.

One advantage of the leg gasketing system 70 of the disposable absorbent articles detailed herein is that when a substantially liquid-impervious material is used in construction of the cuff, the polymeric film layer may be narrowed or not present at all, resulting in more cost effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

In one embodiment of the disposable absorbent articles detailed herein, the backsheet polymeric film is less than about 50 mm wider than the absorbent core; optionally less than about 40 mm wider, less than about 30 mm wider. In one embodiment, the backsheet polymeric film is at least about 20 mm more narrow than the chassis width; optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width.

In one embodiment of the disposable absorbent articles detailed herein, an opacity strengthening patch 80 may be included. The opacity strengthening patch 80 is an additional layer of material. The opacity strengthening patch 80 may be connected to the leg gasketing system 70, the polymeric film layer, or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the leg gasketing system 70 or the polymeric film layer. The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the waist edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis where strength and opacity is desirable. Materials suitable to act as the opacity strengthening patch include materials having a basis weight of at least about 10 gsm, at least about 15 gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers". In some embodiments, the leg gasketing material does not include a polymeric film in its construction.

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the disposable absorbent articles detailed herein, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example. N-fibers are further discussed in WO 2005/095700 and U.S. patent application Ser. No. 13/024,844.

Figure 6:
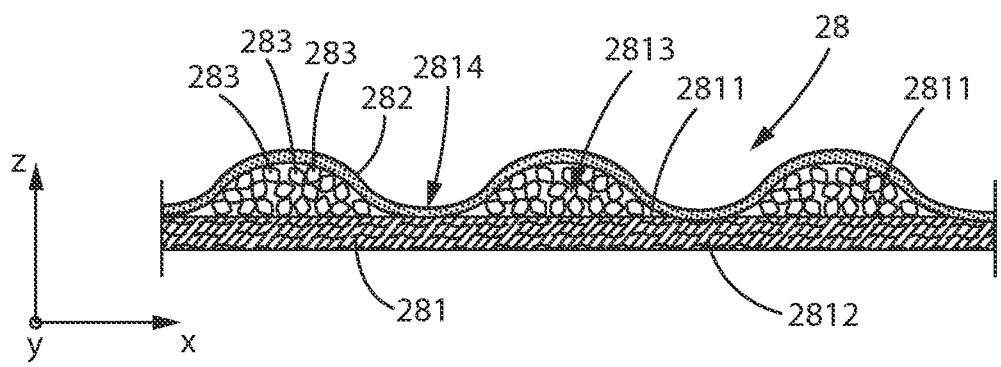
FIG. 6 is a schematic cross section view of an embodiment of an absorbent core suitable for use in the absorbent articles detailed herein.
Figure 7:
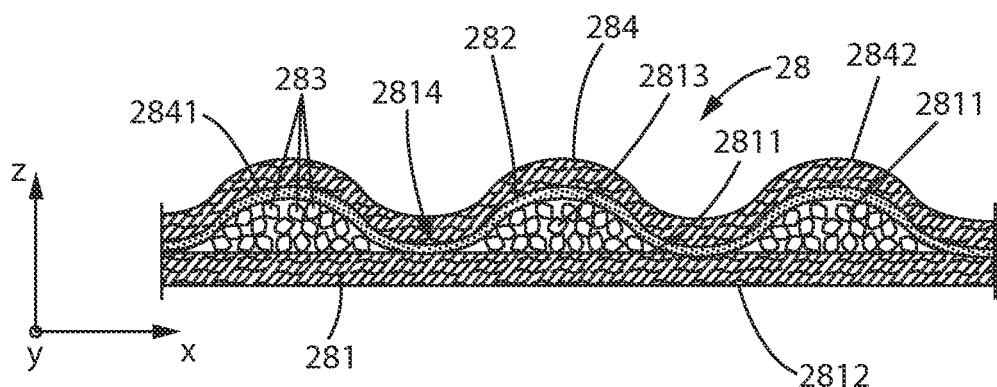
FIG. 7 is a schematic cross section view of an embodiment of an absorbent core suitable for use in the absorbent articles detailed herein.
Figure 8:
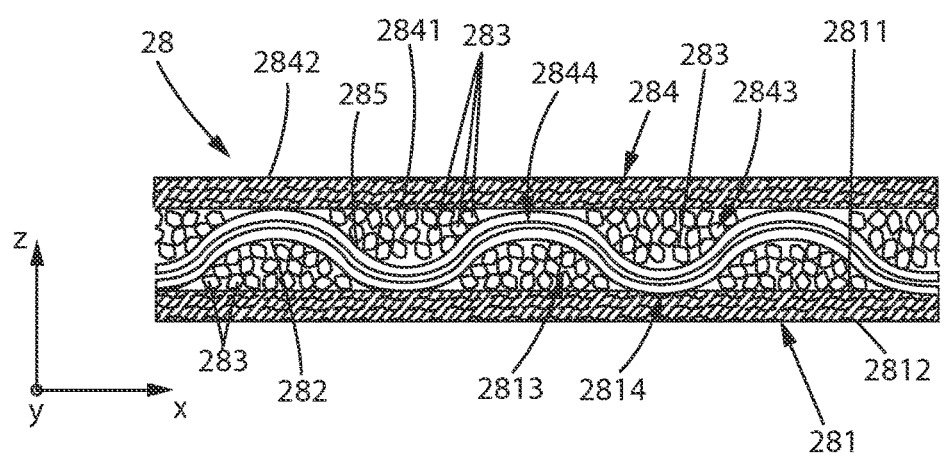
FIG. 8 is a schematic cross section view of an embodiment of an absorbent core suitable for use in the absorbent articles detailed herein.

In one embodiment, an absorbent article includes an absorbent core 28 that is substantially cellulose free, as described in U.S. Pat. Nos. 7,750,203; 7,744,576, and U.S. Patent Publication No. 2008/0312617A1. Cross-sectional views of examples of suitable absorbent cores are schematically represented in FIGS. 6-8. In one embodiment, an absorbent core 28 comprises first and second layers of material 281, 282 and an absorbent material 283 disposed between the first and second layers 281, 282. In one embodiment the first and second layers of material can be a fibrous material chosen from at least one of a nonwoven fibrous web, a woven fibrous web and a layer of thermoplastic adhesive material. Although the first and second layers can be made of a same material, in one embodiment, the first layer 281 is a nonwoven fibrous web and the second layer 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblown fibers. In one embodiment, the nonwoven web 281 can be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer 281 comprises a first surface 2811 and a second surface 2812 and at least regions 2813 of the first surface are in direct facial relationship with a significant amount of absorbent material 283. In one embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material By "direct facial relationship with a significant amount of absorbent material" it is meant that some absorbent material is deposited on top of the regions 2813 at a basis weight of at least 100 g/m$^2$, at least 250 g/m$^2$ or even at least 500 g/m$^2$. The pattern may include regions that all have the same shape and dimensions (i.e. projected surface area and/or height). In the alternative the pattern may include regions that have different shape or dimensions to form a gradient of regions.

In one embodiment, the second layer 282 is a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20 to about 40% by weight. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In exemplary embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0 to about 15%.

The thermoplastic adhesive material 282 can be disposed substantially uniformly within the absorbent material 283. In the alternative, the thermoplastic adhesive material 282 can be provided as a fibrous layer disposed on top of the absorbent material 283 and the regions 2814 of the first surface 2811 that are in facial relationship with only an insignificant amount of absorbent material. In one embodiment, a thermoplastic adhesive material is applied at an amount of between 1 and 20 g/m$^2$, between 1 and 15 g/m$^2$ or even between 2 and 8 g/m$^2$. The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In one embodiment, the absorbent core 28 may further comprise a second layer of a nonwoven fibrous material 284. This second layer may be provided of the same material as the nonwoven fibrous layer 281, or in the alternative may be provided from a different material. It may be advantageous for the first and second nonwoven fibrous layers 281, 284 to be different in order to provide these layers with different functionalities.

The regions 2813 may have any suitable shape in the x-y dimension of the absorbent core. In one embodiment, the regions 2813 form a pattern of disc that are spread on the first surface of the first web 281. In one embodiment, the regions 2813 form a pattern of longitudinal "strips" that extend continuously along the longitudinal axis of the absorbent core (i.e. along the y dimension). In an alternative embodiment, these strips may be are arranged to form an angle of at between 10 and 90 degrees, between 20 and 80 degrees, between 30 and 60 degrees, or even 45 degrees relative to the longitudinal axis of the absorbent article.

In one embodiment, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In one embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In one embodiment, the pattern of absorbent material present on the second nonwoven layer 284 may be the same as the pattern of absorbent material present on the first nonwoven layer 281. In another embodiment, the patterns of absorbent material that are present on the first and second nonwoven layers are different in terms of at least one of the shape of the regions, the projected surface areas of the regions, the amount of absorbent material present on the regions and the type of absorbent material present on the regions.

The absorbent core 28 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01). In one embodiment, the absorbent material 283 is absorbent polymer material which is in particulate form so as to be flowable in the dry state.

EXAMPLES

DIFFERENTIAL CONTRACTION

| Products | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta in Chassis Contraction (%) Delta CC |
|---|---|---|---|---|---|---|---|
| Anerle Diaper (1) | 294 | 330 | 10.91 | 296 | 332 | 10.84 | 0.1 |
| Parents Choice Diaper (2) | 251 | 286 | 12.24 | 247 | 288 | 14.24 | 2.0 |
| Moony Diaper (3) | 202 | 232 | 12.93 | 197 | 238 | 17.23 | 4.3 |
| Huggies Baby Steps (4) | 296 | 340 | 12.94 | 299 | 335 | 10.75 | 2.2 |
| Huggies Supreme (5) | 251 | 270 | 6.91 | 231 | 270 | 14.34 | 7.4 |
| Drypers (6) | 300 | 350 | 14.29 | 284 | 332 | 14.46 | 0.2 |

(1) Anerle Taped Diaper from Philippines, Size L (9-13 kg), SKU 90324495220, Lot 20121009 WP071157C9236; green foam sandwiched waistband
(2) Parents Choice Taped Diaper (2) from North America, Lot 9344 M02 1759 S-1855; white foam sandwiched waistband
(3) Moony Taped Diaper from Japan, Lot 910193071; green foam sandwiched waistband
(4) Huggies Baby Steps US, 1991, Size 4, Lot 3U251910248; white foam sandwiched waistband in blue film
(5) Huggies Supreme 2001, Size 4, Lot NM127501F0755; green nonwoven waistband with small denier elastic strands in white film
(6) Drypers, US, Size Large, Sep. 8, 1998; white foam sandwiched waistband white film

| Examples | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta Chassis Contraction (%) Delta CC |
|---|---|---|---|---|---|---|---|
| A | 171 | 212.2 | 24.1 | 160 | 212.4 | 32.8 | 8.7 |
| B | 175.2 | 212.6 | 21.3 | 165.2 | 212.6 | 28.7 | 7.3 |
| C | 179.6 | 212.6 | 18.4 | 166.2 | 212.6 | 27.9 | 9.5 |
| D | 179.4 | 212.4 | 18.4 | 164.2 | 212.8 | 29.6 | 11.2 |
| E | 191.2 | 212.4 | 11.1 | 163.6 | 212.4 | 29.8 | 18.7 |
| F | 184.6 | 212.2 | 15.0 | 170.6 | 212.6 | 24.6 | 9.7 |
| G | 199.4 | 212.2 | 6.4 | 163.6 | 212.6 | 30.0 | 23.5 |
| H | 192.4 | 212.6 | 10.5 | 165 | 213 | 29.1 | 18.6 |
| I | 201.6 | 212.4 | 5.4 | 165 | 212.4 | 28.7 | 23.4 |
| J | 208.8 | 212.8 | 1.9 | 164.2 | 212.8 | 29.6 | 27.7 |

A - Installed Elongation: 150%; Waistband Strain: 150%; Delta Front/Back Installed Elongation: 0
5B - Installed Elongation: 200%; Waistband Strain: 200%; Delta Front/Back Installed Elongation: 0
C - Installed Elongation: 150%; Waistband Strain: 130%; Delta Front/Back Installed Elongation: 20
D - Installed Elongation: 200%; Waistband Strain: 180%; Delta Front/Back Installed Elongation: 20
E - Installed Elongation: 150%; Waistband Strain: 110%; Delta Front/Back Installed Elongation: 40
F - Installed Elongation: 200%; Waistband Strain: 160%; Delta Front/Back Installed Elongation: 40
10G - Installed Elongation: 150%; Waistband Strain: 100%; Delta Front/Back Installed Elongation: 50
H - Installed Elongation: 200%; Waistband Strain: 140%; Delta Front/Back Installed Elongation: 60
I - Installed Elongation: 200%; Waistband Strain: 120%; Delta Front/Back Installed Elongation: 80
J - Installed Elongation: 200%; Waistband Strain: 100%; Delta Front/Back Installed Elongation: 100

CONSOLIDATION

| Products | Relaxed Caliper (mm) | Extended Caliper (mm) | Extended Length CEL (mm) | Relaxed Length RWL (mm) | Total Length EWL (mm) | Full Waistband Consolidation (%) | Extended Waistband Consolidation (%) |
|---|---|---|---|---|---|---|---|
| Huggies Snug & Dry (7) | 0.91 | 0.55 | 237 | 172 | 273 | 59 | −14 |
| Huggies Little Movers (8) | 1.08 | 0.61 | 223 | 155 | 241 | 56 | −14 |
| Huggies Overnight (9) | 1.45 | 0.70 | 220 | 131 | 253 | 93 | 33 |
| K | 1.64 | 0.40 | 205 | 125 | 201 | 60 | −1 |
| L | 2.24 | 0.71 | 208 | 132 | 286 | 116 | 53 |

-continued

CONSOLIDATION

| Products | Relaxed Caliper (mm) | Extended Caliper (mm) | Extended Length CEL (mm) | Relaxed Length RWL (mm) | Total Length EWL (mm) | Full Waistband Consolidation (%) | Extended Waistband Consolidation (%) |
|---|---|---|---|---|---|---|---|
| M | 2.40 | 1.04 | 203 | 130 | 340 | 162 | 98 |
| N | 2.54 | 1.01 | 205 | 131 | 386 | 195 | 131 |
| O | 2.22 | 1.29 | 205 | 126 | 425 | 237 | 176 |

(7) Huggies Snug & Dry, size 4; Lot No. BI 103108B
(8) Huggies Little Movers, size 3; Lot No. BI 024610B
(9) Huggies Overnight, size 4; Lot No. PA 027104F
K - 75% Installed Elongation and 75% Waistband Strain
L - 150% Installed Elongation and 75% Waistband Strain
M - 225% Installed Elongation and 75% Waistband Strain
N - 300% Installed Elongation and 75% Waistband Strain
O - 375% Installed Elongation and 75% Waistband Strain

360 LEAKAGE PROTECTION

| Products | Average Leg Gasketing System Gather Count | Average Waistband Gather Count | Ratio of Leg Gasketing System Gather Count to Waistband Gather Count |
|---|---|---|---|
| P | 20.7 | 22.2 | 0.9 |
| Q | 21.2 | 21.2 | 1.0 |
| R | 16.7 | 18.2 | 0.9 |
| Huggies Baby Steps (4) | 23.2 | 12.5 | 1.9 |
| Huggies Supreme (5) | 17.0 | 24.0 | 0.7 |
| Anerle Diaper (1) | 20.0 | 16.0 | 1.3 |
| Parent Choice (2) | 20.0 | 15.5 | 1.3 |
| Moony Diaper (3) | 12.5 | 11.2 | 1.1 |

P—150% Installed Elongation, 75% Waistband Strain
R—150% Installed Elongation, 75% Waistband Strain
Q—150% Installed Elongation, 75% Waistband Strain Stiffness and Resiliency for First Waist Region

| Products | Stiffness (N) | Resiliency (mJ) |
|---|---|---|
| S | 7.6 | 6.5 |
| T | 2.2 | 1.3 |
| U | 11.9 | 16.1 |
| V | 2.5 | 0.8 |
| W | 3.5 | 4.7 |
| X | 3.6 | 1.8 |

S—Exemplary First Waist Region with a waistband of the following construction: A 30 gsm side-by-side bi-component polyethylene/polypropylene non-woven with a wavy bond pattern (the details of the pattern can be found in US2010298796). The bond is about 1 mm wide, the unbonded region is about 2.5 mm wide, wave amplitude is about 4 mm, and wave frequency is about 0.04 mm$^{-1}$. Elastic installed elongation is 90%, and applied waistband strain is 11%. All waistband adhesives are spiral glue.
T—Typical First Waist Region with a waistband of the following construction: A 10 gsm SMS non-woven with a bond pattern consisting of small dots. Elastic installed elongation is 90%, and Applied WB Strain is 11%. All waistband adhesives are spiral glue.
U—Stiff First Waist Region with a waistband of the following construction: A 45 gsm side-by-side bi-component polyethylene/polyamide non-woven with through-air bonding (no bond pattern). Elastic installed elongation is 90%, and applied waistband strain is 11%. All waistband adhesives are spiral glue.
V—Foam First Waist Region is from a size 4 Mamy Poko Boy/Girl taped diaper from China
W—Intermediate First Waist Region with a waistband of the following construction: A 24 gsm highloft through-air bonded PE/PET (no bond pattern). Elastic installed elongation is 90%, and applied waistband strain is 11%. All waistband adhesives are spiral glue.
X—Low Resiliency First Waist Region with a waistband of the following construction: A 15 gsm side-by-side bi-component polyethylene/polyamide non-woven with a wavy bond pattern (the details of the pattern can be found in US2010298796). The bond is about 1 mm wide, the unbonded region is about 2.5 mm wide, wave amplitude is about 4 mm, and wave frequency is about 0.04 mm$^{-1}$. Elastic installed elongation is 90%, and applied waistband strain is 11%. All waistband adhesives are spiral glue.

MAXIMUM DIFFERNECE IN RESILIENCY BETWEEN TWO ADJACENT SECTIONS

| Products | Stiffness (N) | Maximum Δ Resiliency Between Two Adjacent Sections (%) |
|---|---|---|
| S | 7.6 | 41.4 |
| T | 2.2 | 149.3 |
| U | 11.9 | 47.1 |
| V | 2.5 | 428.6 |
| W | 3.5 | 108.6 |
| X | 3.6 | 254.3 |

S—Exemplary First Waist Region (same as Product S above in the Stiffness and Resiliency data)
T—Typical First Waist Region (same as Product T above in the Stiffness and Resiliency data)
U—Stiff First Waist Region (same as Product U above in the Stiffness and Resiliency data)
V—Foam First Waist Region (same as Product V above in the Stiffness and Resiliency data)
W—Intermediate First Waist Region (same as Product W above in the Stiffness and Resiliency data)
X—Low Resiliency First Waist Region (same as Product X above in the Stiffness and Resiliency data)

CORRUGATION REGULARITY IN THE WAIST ASSEMBLY

| Products | Average Gather Spacing (mm) | Gather Spacing Standard Deviation (mm) | Percentage less than 1 mm from Average (%) |
|---|---|---|---|
| Y | 2.77 | 0.52 | 95.5 |
| Z | 3.67 | 1.23 | 63.3 |

Y—Exemplary First Waist Region with a waistband of the following construction: A 30gsm side-by-side bi-component polyethylene/polypropylene non-woven with a wavy bond pattern (the details of the pattern can be found in US2010298796). The bond is about 1 mm wide, the unbonded region is about 2.5 mm wide, wave amplitude is about 4 mm, and wave frequency is about 0.04 mm$^{-1}$. Elastic installed elongation is 90%, and applied waistband strain is 11%. All waistband adhesives are spiral glue.
Z—Typical First Waist Region with a waistband of the following construction: A 10gsm SMS non-woven with a bond pattern consisting of small dots. Elastic installed elongation is 90%, and applied waistband strain is 11%. All waistband adhesives are spiral glue.

CORRUGATION UNIFOMRITY IN THE WAIST ASSEMBLY

| Products | No. of Complete Gathers | No. of Broken Gathers | Percentage of Gathers that are Complete (%) |
|---|---|---|---|
| Y | 40 | 8 | 83.3 |
| Z | 10 | 22 | 31.3 |

Y—Exemplary First Waist Region (same as Product Y above in the Corrugation Regularity data)
Z—Typical First Waist Region (same as Product Z above in the Corrugation Regularity data)

Test Methods

Chassis Contraction Method

The chassis contraction is measured using a calibrated ruler capable of measuring to ±1 mm, (traceable to National standards such as NIST), and a force gauge capable of measuring an applied force of 500 g accurately to ±0.5 g (a suitable gauge is the Chatillon DFS series, available from Ametek, Largo, Fla.). A spring loaded clamp, with contact faces 60 mm wide by 10 mm deep, is attached to the force gauge to hold the test article. All testing is performed in a room maintained at about 23±2° C. and about 50±2% relative humidity. All samples were conditioned for 2 hours before testing at about 23±2° C. and about 50±2% relative humidity.

For this measure the chassis is identified as the portion of the article with contiguous back sheet and does not include any attached tabs or attached elastic tabs/ears. Unfold the absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. With the article flat against the bench, lay the calibrated ruler along the article aligning it with the lateral midline of the waist feature. Measure the lateral distance from the right distal edge of the chassis to the left distal edge of the chassis and record to the nearest 1 mm. This is the Relaxed Back Chassis Width (RBCW).

Attach the force gauge to the right distal edge of the chassis. As attached, the force gauge is oriented to pull from left to right. The grip faces are parallel to the longitudinal axis of the article, centered at the lateral midline of the waist feature, with 3 mm of the chassis within the grip faces.

Adhere a piece of 2-sided adhesive tape 50 mm in width by 900 mm long to the bench. Hold the article with the back sheet directed toward the taped surface with the back waist parallel to the long dimension of the tape. Align the lateral midline of the waist feature with the lateral midline of the tape strip. Secure the first 3 mm of the left chassis edge to the adhesive tape. Using the force gauge, extend the back waist to an applied force of 500 g. Next, lower the article and adhere the article's back waist to the adhesive tape across the lateral width of the chassis. Remove the force gauge from the chassis. Lay the ruler across the article aligning it along the lateral midline of the waist feature. Measure the lateral distance from the right distal edge of the chassis to the left distal edge of the chassis and record to the nearest 1 mm. This is the Extended Back Chassis Width (EBCW).

Repeat this measure in like fashion for the front waist feature of the article to determine the Relaxed Front Chassis Width (RFCW) and the Extended Front Chassis Width (EFCW). Calculate the Chassis Contractions as follows:

% Back Chassis Contraction (% BCC)=(EBCW−RBCW)/EBCW×100

% Front Chassis Contraction (% FCC)=(EFCW−RFCW)/EFCW×100

Front-to-Back Delta Chassis Contraction=absolute value of (% BCC−% FCC)

Waist Feature Calipers

Calipers were performed using an Ono Sokki digital caliper (GS-503 Linear Gauge Sensor with DG-3610 Digital Gauge, Ono Sokki Co, Japan) capable of measuring to 0.01 mm. The foot diameter is 1 cm and the applied pressure is 0.5 psi. Readings are taken after a residence time of 5 sec. Linear measurements are made using a calibrated ruler capable of measuring to ±1 mm (traceable to National standards such as NIST). A stainless steel plate, uniformly 1.5 mm thick±0.1 mm, 20 cm wide and 40 cm long is used for mounting the extended waist. All testing is performed in a room maintained at about 23±2° C. and about 50±2% relative humidity. All samples are conditioned for 2 hours before testing at about 23±2° C. and about 50±2% relative humidity.

Relaxed Waist Calipers

Unfold an absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its longitudinal midline. This is the Relaxed Length of the waist feature (RWL) Mark the waist feature along its midline at 50% of its lateral width. This is waist site 1 (WS1). Measure and mark two more sites, the first 1.5 cm to the left of the 50% mark (WS2) and the second 1.5 cm to the right of the 50% mark (WS3).

Place the caliper on the anvil and zero the digital controller. Place the article on the anvil, with the top sheet facing upward, and use the caliper to measure the thickness at WS1, WS2, and WS3. Report to the nearest 0.01 mm as the Relaxed Waist Caliper RWC1, RWC2, and RWC3 respectively.

Using a cryogenic freeze spray (available as CytoFreeze, Control Company, TX) gently remove the elastic feature from the article. Place the article on the anvil, with the top sheet facing upward, and use the caliper to measure the thickness of the article corresponding to WS1, WS2, and WS3. Report to the nearest 0.01 mm as Relaxed Back Sheet Caliper RBC1, RBC2, RBC3 respectively.

Calculate the Waist Feature Caliper as:

Relaxed Waist Feature Caliper=[(RWC1−RBC1)+(RWC2−RBC2)+(RWC3−RBC3)]/3.

Repeat this procedure for three identical articles and report as the average to the nearest 0.01 mm.

Extended Waist Calipers

Unfold an absorbent article taking care not to stretch the waist features. Assemble a vertical ring stand which supports a horizontal bar. Attach a spring loaded clamp to the left edge of the chassis, centered on the waist feature. Attach the clamp to the horizontal support so that the waist feature hangs vertically. Attach a second clamp, which has a mass of 300 g±1 g, to the right edge of the chassis, centered on the midline of the waist feature. Allow the article to hang for 30 seconds and then using the calibrated ruler measure the extended length of the waist feature to the nearest 1 mm. This is the Chassis Extended Length (CEL). The CEL can be used for all extended waist measures.

Unfold another absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its longitudinal midline. This is the Relaxed Length of the waist feature (RWL) Mark the waist feature along its midline at 50% of its lateral width. This is waist site 1 (WS1). Measure and mark two more sites, the first 1.5 cm to the left of the 50% mark (WS2) and the second 1.5 cm to the right of the 50% mark (WS3). Identify the proximal edge of the waist feature, i.e. the edge closest to the crotch of the article. Mark a lateral line 1.5 cm from the proximal edge toward the crotch, and parallel to the waist feature. Along a longitudinal axis that passes through WS1, mark the intersection at the lateral line just drawn (AS1). Repeat in like fashion for WS2 and WS3 to define sites AS2 and AS3 respectively.

Place the article, top sheet facing upward, onto the stainless steel plate. Secure the left distal edge of the chassis at the waist feature's midline to the steel plate with adhesive tape. Grasp the right side of the chassis and pull until the waist feature has been extended equal to the Chassis Extended Length (CEL). Secure the right side of the chassis to the steel plate with adhesive tape.

Place the steel plate with attached article on the anvil of the caliper. Place the caliper foot on a region of the steel plate that is not covered by the article and zero the digital control Using the caliper, measure the thickness at the six marked sites. Report to the nearest 0.01 mm as Extended Waist Caliper EWC1, EWC2, and EWC3. Using a cryogenic freeze spray gently remove the elastic feature from the article. Place the steel plate with attached article on the anvil of the caliper and measure the thickness of the article at the sites corresponding to WS1, WS2 and WS3. Report to the nearest 0.01 mm as Extended Back Sheet Caliper EBC1, EBC2, EBC3 respectively.

Calculate the Waist Feature Calipers as:

Extended Waist Feature Caliper=[(EWC1−EBC1)+ (EWC2−EBC2)+(EWC3−EBC3)]/3

Repeat this procedure for three identical articles and report as the average to the nearest 0.01 mm.

Waist Feature Percent Consolidation

Linear measurements are made using a calibrated ruler capable of measuring to ±1 mm (traceable to National standards such as NIST). All testing is performed in a room maintained at about 23±2° C. and about 50±2% relative humidity. All samples are conditioned for 2 hours before testing at about 23±2° C. and about 50±2% relative humidity.

Unfold the absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its midline and record to the nearest 1 mm. This is the Relaxed Length of the waist feature (RWL).

Using a cryogenic freeze spray (available as CytoFreeze, Control Company, TX) carefully remove the waist feature from the article. Place the waist feature into a beaker with 100 mL of dichloromethane and soak for 15 minutes to dissolve the adhesives. Remove the waist feature from the solvent and remove the elastics. Lay the waist feature substrate flat in a fume hood to dry. Assemble a vertical ring stand which supports a horizontal bar. Attach a spring loaded clamp, which is at least as wide as the waist feature, to the left edge of the waist feature. Attach the clamp to the horizontal support so that the waist feature hangs vertically. Attach a second clamp, which has a mass of 3 g±1 g and is at least as wide as the waist feature, to the right edge of the waist feature. Allow the article to hang for 30 seconds and then using the calibrated ruler measure the extended length of the waist feature to the nearest 1 mm. This is the Extended Waist Feature Length (EWL).

Calculate the Full Waistband Consolidation as:

% Full Waistband Consolidation=(EWL−RWL)/ RWL×100

Repeat this procedure for three identical articles and report as the average to the nearest 1 mm.

Calculate the Extended Waistband Consolidation as:

% Extended Waistband Consolidation=(EWL−RWL)/ RWL×100−(1−((CEL−RWL)/CEL)*100)

Repeat this procedure for three identical articles and report as the average to the nearest 1 mm.

Frequency of Waistband and Outer Leg Cuff Gathers on Taped Diaper Products

The frequency of gathers for the waistband and outer leg cuffs is performed using a template (FIG. 10) with manual counting of the gathers. The template is 25 mm wide by 80 mm long by 6 mm thick with a 5 mm wide by 30 mm long window centered in the template. A lip 6 mm wide by 80 mm long by 6 mm thick is attached flush to the back edge of the template. Taking care not to stretch the waistband, place the article on a horizontal bench with the backsheet facing downward. Referring to FIG. 3, visually identify the CD and MD center of the waistband 2000 on the article. Place the template on top of and parallel to, the waistband with the midpoint centered in the window. Manually count and record the number of gathers visible in the window. Again, taking care not to stretch the waistband, turn the article over such that the topsheet is now facing downward. Visually identify the CD and MD center of the waistband. Place the template on top of and parallel to, the waistband with the midpoint centered in the window. Manually count and record the number of gathers visible in the window. In like fashion repeat these two measures for the waistband 1000. Average the four values and report to the nearest 0.1 gather per 30 mm.

Taking care not to stretch the Leg Gasketing System, place the article on a horizontal bench with the backsheet facing downward. Referring to FIG. 3, visually identify the CD and MD center of the Leg Gasketing System gather 70 on the article. Place the template on top of, and parallel to, the left Leg Gasketing with the midpoint centered in the window. Manually count and record the number of gathers visible in the window. In like fashion repeat for the right Leg Gasket. Average the two values and report to the nearest 0.1 gather. Average the two values and report to the nearest 0.1 gather per 30 mm.

Calculate the Ratio of Leg Gasketing System Gather Count to Waistband Gather Count as follows:

Ratio=Average Leg Gasketing System Gather Count/ Average Waistband Gather Count

Repeat this procedure for three identical articles and report as the average to the nearest 0.01 units CD Length Ratio CD Length Ratio is the ratio of chassis extended length (CEL) to Extended Back Chassis Width (EBCW), as defined here.

Calculate the CD Length Ratio as follows:

CD Length Ratio=CEL/EBCW

Repeat this procedure for three identical articles and report as the average.

First Waist Region Stiffness and First Waist Region Resiliency Method

First waist region stiffness and first waist region resiliency are measured using a constant rate of extension tensile tester with computer interface (a suitable instrument is a MTS Insight Model 1 EL under Test Works 4 software, as available from MTS Systems Corp., Eden Prairie, Minn.) fitted with a 25 N load cell. A plunger 300 shown in FIG. 20 and also FIG. 21 (rotated 90 degrees) is used for the upper movable test fixture and a support platform 310 is used as the lower stationary test fixture. All testing is performed in a conditioned room maintained at 23° C.±2 C.° and 50%±2% relative humidity.

The foot component 301 of the plunger 300 is made of two smooth Plexiglas sheets 302 and 303, 12 mm thick to maximize the available load cell capacity. The shaft 304 is machined to fit the tensile tester and has a locking collar 305 to stabilize the plunger and maintain alignment orthogonal to the test surface 311 of the base support platform 310. The foot 301, is 300 mm deep by 50 mm high by 50 mm wide, and creates a right angle 306 with minimal radius on the material contacting surface 307. The foot 301 is secured to the shaft 304 such that the bottom edge 308 of the foot is parallel to the surface of the test surface 311.

The bottom fixture 310 is attached to the tensile tester with the shaft 314 machined to fit the tensile tester and locking collar 315. The laterally movable support platform 312 is mounted on a rail 313 and has a set screw 316 to lock its position after adjustment. The test surface 311 is made from polished aluminum 500 mm wide by 300 mm deep and is attached to the top of the platform 312. The platform 312 extends 100 mm above the top surface of rail 313.

Samples are conditioned at 23° C.±2 C.° and 50%±2% relative humidity for 2 hours prior to testing. Four (4) patches of double sided adhesive tape (e.g. 3M Brand tape available from 3M, St. Paul, Minn.) are adhered to the garment facing surface of the article to attach the specimen to the testing platform 311. Place the article, back sheet facing upward, onto a lab bench. At the waist to be tested, extend the article in the lateral direction until the article is laid flat. Secure the extended article to the bench. Starting at the waist edge 321, measure down the lateral edge 350 the specified distance (e.g., 15 mm inboard of the waist edge, or 10 mm inboard of the waist edge, etc.) and mark. Repeat for the opposing lateral edge. Draw a line 322 across the back of the article connecting these two points. At the left edge 350 place a patch of adhesive tape 15 mm wide by 30 mm long with its long edge flush with the article edge 350 and its width edge extending inboard from the line 322. Repeat in like fashion for the right lateral edge of the article. From the longitudinal centerline 100 of the article, measure 26 mm laterally toward the left distal edge of the article and mark (distance 325). Place another 15 mm×30 mm patch of adhesive tape with its length edge parallel to the longitudinal axis of the product and its width edge extending inboard from the line 322. Repeat in like fashion for the right side of the article. Set the gage height (distance 317a) such that bottom surface 308 of the plunger foot 301 is 5.00±0.01 mm above the top plane of the test surface 311. Set the position of the platform 312 such that nearest surface of foot 301 is offset 5.00 mm±0.01 mm away from the side edge of the testing surface 318 (distance 317). Program the tensile tester to complete the following steps 5 times: execute an extension cycle by lowering the crosshead downward 15.00 mm at a rate of 51 mm/min while collecting displacement and force data at a rate 100 Hz; wait 2 seconds after completing the extension cycle; execute a relaxation cycle by raising the crosshead upward 15.00 mm at a rate of 51 mm/min while collecting displacement and force data at a rate of 100 Hz; wait 30 seconds after completing the relaxation cycle.

Figure 22:
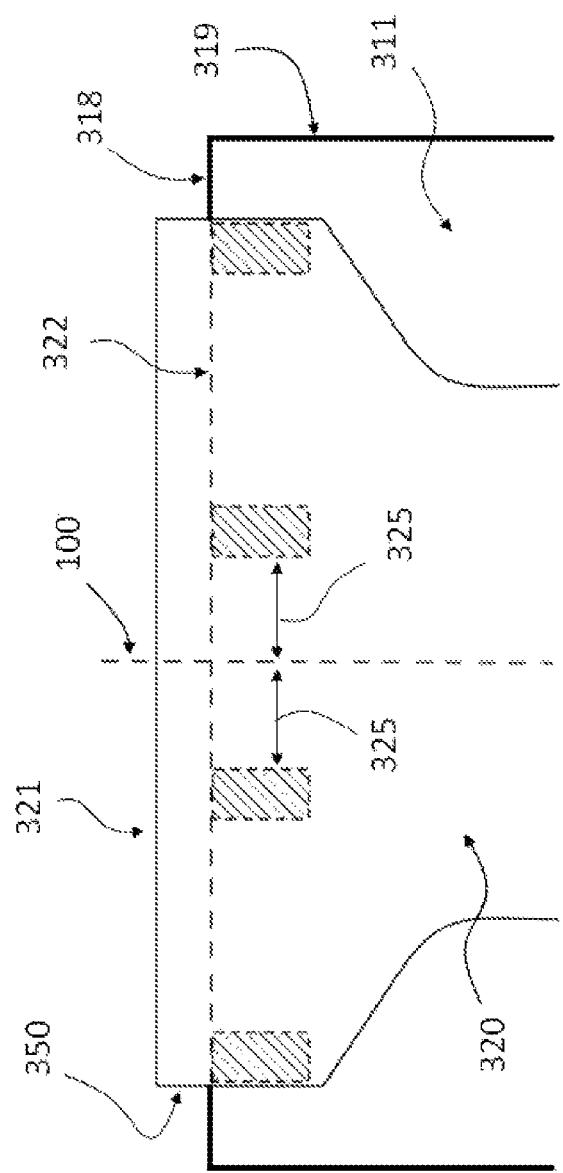
FIG. 22 is a schematic representation of exemplary specimen secured to the testing surface of the apparatus illustrated in FIGS. 20 and 21.

Referring to FIGS. 20 and 22, the article is adhered to the test surface 311 garment-facing surface downward using the 2-sided tape just applied. With the article still fully extended, align the longitudinal centerline of the article with the center of the foot 301, and line 322 aligned with the edge of the test surface 311. Keeping this alignment, lower and adhere the article onto the test surface 311. If the front waist edge 321 can be adjusted to present either a convex or concave surface to the bottom face 308 of plunger 301 after being attached, arrange the waist edge 321 to present a concave surface relative to the test edge 318 of the test surface 311. Arrange the rest of the specimen 320 on the test surface 311 such that any longitudinal contraction in the article (e.g., contraction from leg cuff elastics) causes folds 323,324 to form away from the test surface 311. Ensure all materials in the article are lying in a flat out state up to fold 324 such that no material is flipped over, bent, or twisted. Ensure all portions of the specimen 320, other than the portions between the marked location 322 and the waist edge 321, will not interfere with the motion of the plunger. A weighted block 330 may be used to hold the back of the article out of the way of the plunger.

Figure 23:
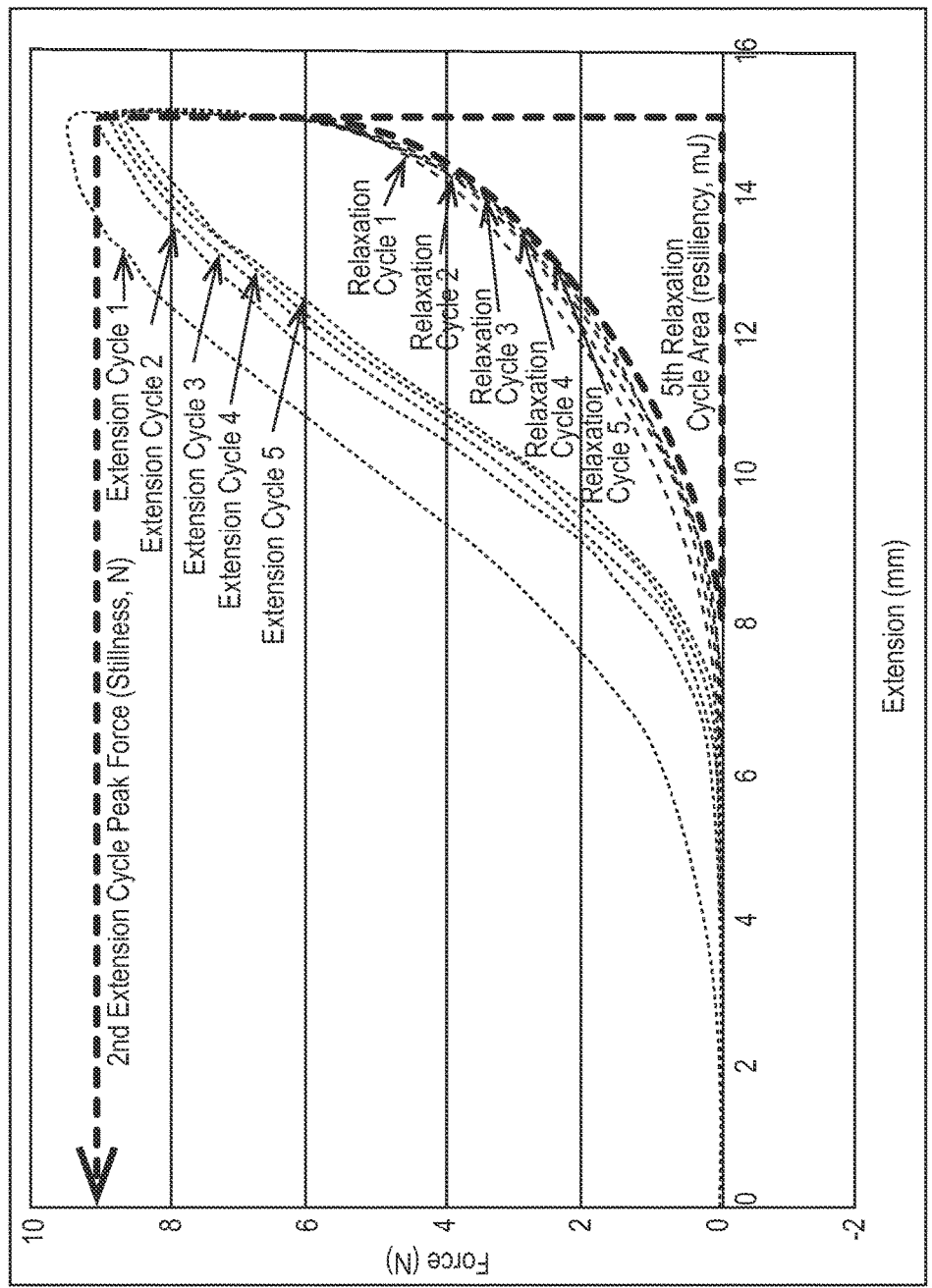
FIG. 23 is an exemplary graph charting the data generated by the Test Works 4 software when being used for resiliency and stiffness measurements.

Zero the load cell and the crosshead position. Start the test and collect data. An exemplary chart created by Excel utilizing the raw data generated by the Test Works 4 software is shown in FIG. 23. From the resulting force (N) verses displacement curves (mm) calculate the Peak Force (N) during the second extension cycle and report to the nearest 0.1N. Also, calculate the Area (mJ) under the fifth relaxation cycle and report to the nearest 0.1 mJ. Repeat the test for a total of 15 substantially identical articles. Report the Waist Region Stiffness as an average of the Peak Force (from $2^{nd}$ cycle) of the 15 replicates to the nearest 0.1 N. Report the Waist Region Resiliency as an average of the Area of the 15 replicates to the nearest 0.1 mJ.

Regularity and Uniformity Methods for Waist Assembly Corrugations

Corrugation Regularity

Draw a line across the product at the edge of the second section in the first waist region. The line should be parallel to the waist edge, and 15 mm inboard of the waist edge. Follow the drawn line from one longitudinal edge of the product to the opposite longitudinal edge of the product. For each corrugation apex encountered traversing the drawn line (i.e., a location where the product is deformed in the z-direction, and said deformation reaches a vertical apex with respect to the adjacent vertical deformations along the drawn line), measure the distance in millimeters from the current corrugation apex to the next corrugation apex along the drawn line. Record each of these individual distances in millimeters. Average all individual distances. For each individual distance, calculate the absolute value of the difference between the individual distance and the average of all individual distances. Calculate the percentage of differences which are less than 1 mm. Record this percentage as the Corrugation Regularity.

Corrugation Uniformity

Draw a line across the product at the inboard edge of the waist assembly in the first waist region. If there is no waistband or the waistband of the product is more than 25 mm long, the line should be parallel to the waist edge, and 25 mm inboard of the waist edge. If the waistband is less than 25 mm long, the line should be drawn at the inboard edge of the waistband. Follow the waist edge 14 of the first waist region 36 from one longitudinal edge of the product to the opposite longitudinal edge of the product. Count each corrugation apex (i.e., a location where the product is deformed in the z-direction, and said deformation reaches a vertical apex with respect to the adjacent vertical deformations) along the waist edge, and record the total number of corrugation apexes. For each corrugation apex encountered along the waist edge 14, follow the path of the ridge stemming from the corrugation apex longitudinally inboard. A ridge is defined as a longitudinally running continuous series of local high points in the z-direction which meet the definition of a vertical apex at any point along its length by drawing an intersecting line parallel to the waist edge. If the ridge is broken (i.e., reaches a location where the ridge can no longer be followed because it no longer fits its definition of a single ridge) prior to reaching the drawn line, record this as a broken corrugation. If the ridge splits in to two or more paths where each path meets the definition of a ridge prior to reaching the drawn line, record this as a broken corrugation. If the ridge joins with a ridge of a previously counted corrugation apex prior to reaching the drawn line, record this as a broken corrugation. If the ridge reaches the drawn line without any of the aforementioned results, record this as a complete corrugation. Calculate the percentage of complete corrugations in relation to the total number of corrugation apexes. Record this percentage as the Corrugation Uniformity.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the disposable absorbent articles detailed herein. To the extent that any meaning or definition of a term in this written document conflicts with any meaning or definition of the term in a document incorporated by reference, the meaning or definition assigned to the term in this written document shall govern.

While particular embodiments of the disposable absorbent articles detailed herein have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An open form disposable absorbent article comprising: a chassis comprising a topsheet, a backsheet and an absorbent core disposed between the topsheet and the backsheet; a first waist region, a second waist region, a crotch region disposed between the first waist region and second waist region, a waist edge in the first waist region, at least one waistband laminate discretely applied to the chassis on a body-facing surface in the first waist region adjacent the waist edge, the waistband laminate comprising a nonwoven material and an elastic member, and having an inboard edge, wherein a waist assembly is defined between the waist edge and the inboard edge; and at least one fastener in the second waist region, wherein the waistband laminate overlaps the absorbent core, and wherein the waist assembly has a Corrugation Regularity greater than about 75%.

2. The open form disposable absorbent article of claim 1, wherein the Corrugation Regularity is greater than about 80%.

3. The open form disposable absorbent article of claim 1, wherein the Corrugation Regularity is greater than about 90%.

4. The open form disposable absorbent article of claim 1, wherein the nonwoven material has a basis weight of about 30 gsm.

5. The open form disposable absorbent article of claim 1, wherein the open form disposable absorbent article comprises an ear comprising a zero strain stretch laminate.

6. The open form disposable absorbent article of claim 1, wherein the first waist region has a stiffness of less than 8.5 N.

7. The open form disposable absorbent article of claim 1, wherein the waistband laminate is coterminous with the waist edge of the first waist region.

8. The open form disposable absorbent article of claim 1, wherein the open form disposable absorbent article includes a leg gasketing system, and the waistband laminate overlaps the leg gasketing system.

9. The open form disposable absorbent article of claim 8, wherein the waistband laminate laterally terminates within the span of the leg gasketing system.

10. The open form disposable article of claim 8, wherein the leg gasketing system does not include a polymeric film.

11. The open form disposable article of claim 8, wherein the leg gasketing system comprises an N-fiber material.

12. The open form disposable absorbent article of claim 1, wherein the waistband laminate comprises at least two elastic strands.

13. The open form disposable absorbent article of claim 1, wherein the waistband laminate comprises at least three elastic strands.

14. The open form disposable absorbent article of claim 12, wherein at least one of the elastic strands is round in cross section.

15. The open form disposable absorbent article of claim 12, wherein the nonwoven material and the least two elastic strands are combined under a first strain and the waistband laminate is attached to the open form disposable absorbent article under an applied waistband strain, wherein the difference between the first strain and the applied waistband strain results in a waistband having a Full Waistband Consolidation of greater than 40%.

16. The open form disposable absorbent article of claim 1, wherein the waistband laminate comprises crimped or curled fibers.

17. The open form disposable absorbent article of claim 1, wherein the waistband laminate is bonded to the first waist region by glue, thermal bonds, or compression welds.

18. The open form disposable absorbent article of claim 1, wherein the nonwoven material comprises a bond pattern that repeats in a lateral direction, and wherein the bond pattern runs in a longitudinal direction.

19. The open form disposable absorbent article of claim 1, wherein the second waist region comprises a second waistband laminate.

20. The open form disposable absorbent article of claim 1, wherein the waistband laminate does not comprise foam.

21. The open form disposable absorbent article of claim 1, wherein the open form disposable absorbent article comprises an opacity strengthening patch.

22. An open form disposable absorbent article comprising: a chassis comprising a topsheet, a backsheet and an absorbent core disposed between the topsheet and the backsheet; a first waist region, a second waist region, a crotch region disposed between the first waist region and second waist region, a waist edge in the first waist region, at least one waistband laminate discretely applied to the chassis on a body-facing surface in the first waist region adjacent the waist edge, the waistband laminate comprising a nonwoven material and an elastic member, and having an inboard edge, wherein a waist assembly is defined between the waist edge and the inboard edge; and at least one fastener in the second waist region, wherein the waistband laminate overlaps the absorbent core, and wherein the waist assembly has a Corrugation Uniformity of greater than about 50%.

23. The open form disposable absorbent article of claim 22, wherein the waist assembly has a Corrugation Uniformity of greater than about 60%.

24. The open form disposable absorbent article of claim 22, wherein the waist assembly has a Corrugation Uniformity of greater than about 70%.

25. The open form disposable absorbent article of claim 22, wherein the waistband laminate comprises at least two elastic strands.

* * * * *